United States Patent [19]

Koukline

[11] Patent Number: 5,782,397
[45] Date of Patent: Jul. 21, 1998

[54] STAPLING DEVICE

[75] Inventor: Alexandre Koukline, Moscow, Russian Federation

[73] Assignee: Alpha Surgical Technologies, Inc., Rego Park, N.Y.

[21] Appl. No.: 666,314

[22] PCT Filed: Jan. 4, 1995

[86] PCT No.: PCT/US95/00112

§ 371 Date: Aug. 30, 1996

§ 102(e) Date: Aug. 30, 1996

[87] PCT Pub. No.: WO95/18572

PCT Pub. Date: Jul. 13, 1995

Related U.S. Application Data

[63] Continuation-in-part of Ser. No. 177,262, Jan. 4, 1994, abandoned.

[51] Int. Cl.$^6$ ................................. A61B 17/068
[52] U.S. Cl. .............. 227/176.1; 227/19; 227/119; 227/120; 606/219
[58] Field of Search ................ 227/19, 175.1, 227/176.1, 180.1, 119, 120; 128/4; 606/219

[56] References Cited

U.S. PATENT DOCUMENTS

| | | | |
|---|---|---|---|
| 5,009,356 | 4/1991 | Rothfuss et al. | 227/120 |
| 5,174,487 | 12/1992 | Rothfuss et al. | 227/176.1 |
| 5,197,649 | 3/1993 | Bessler et al. | 227/180.1 |

*Primary Examiner*—Scott A. Smith
*Attorney, Agent, or Firm*—Steven M. Hoffberg

[57] ABSTRACT

The stapler includes a staple advancing system for applying an advancing force to a plurality of "U" shaped staples (19); a guide (16) for maintaining said plurality of "U" shaped staples (19) parallel to each other along a feed axis, said guide (35) having a channel cross section (33) including a horizontal top portion, substantially perpendicular to said feed axis, and two semi-vertical portions (37) below said horizontal top portion, each having a plane oriented downwardly inward at such an angle which does not cause plastic deformation of said "U" shaped staples (19) inserted in said guide (35), said guide (35) having an open end wherein said semivertical portions (37) merge with vertical portions (39) having walls which are substantially vertically aligned; a lower aperture (6) aligned along said feed axis with said vertically aligned walls; and a displaceable staple ejector (2) without displacing an adjacent "U" shaped staple (19).

19 Claims, 16 Drawing Sheets

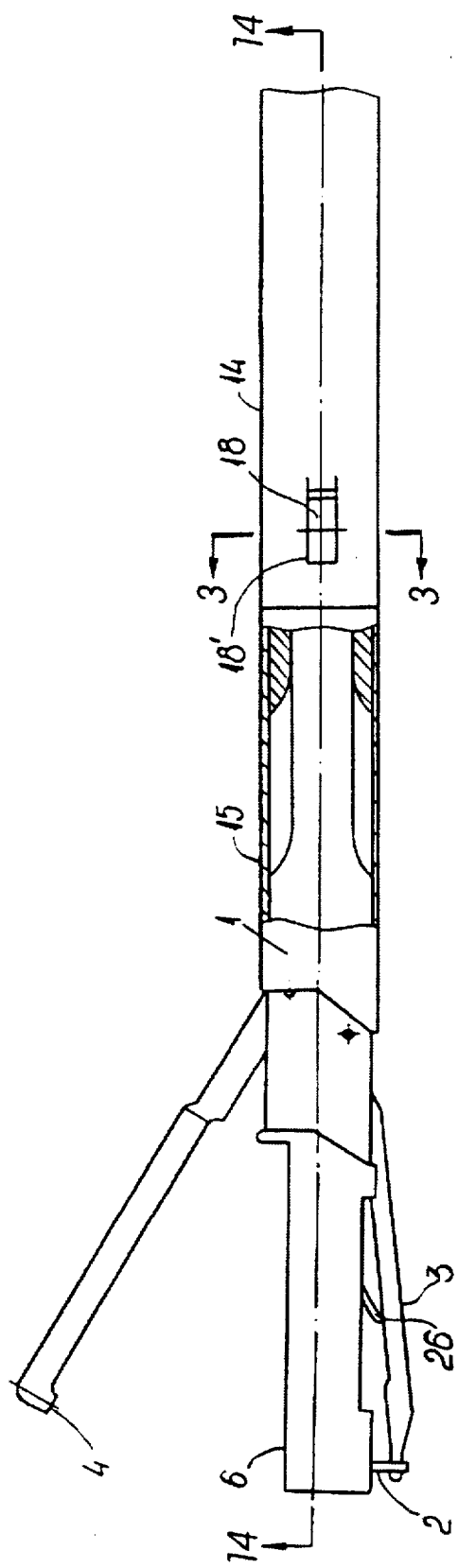
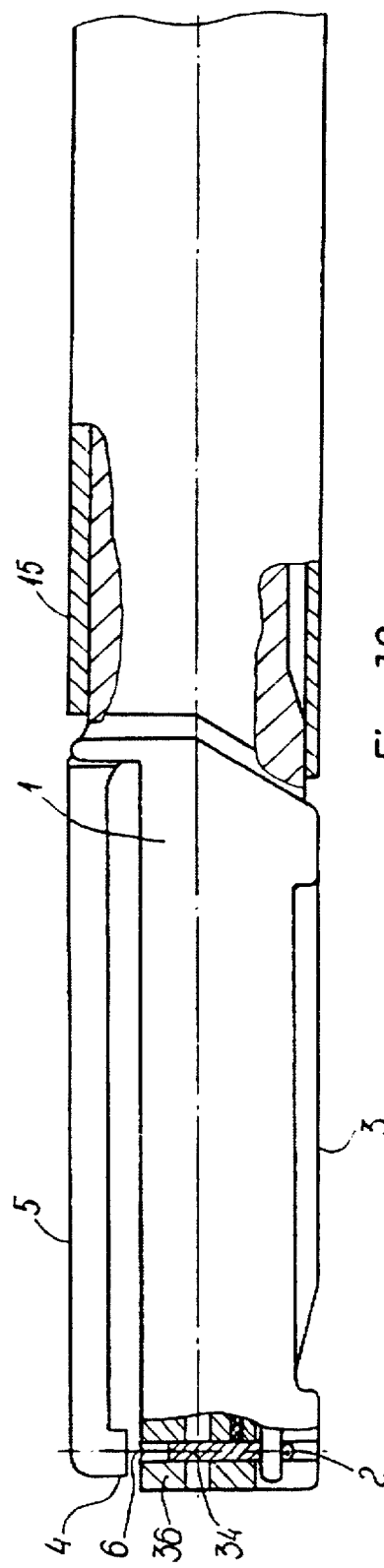
Fig. 12
Fig. 13

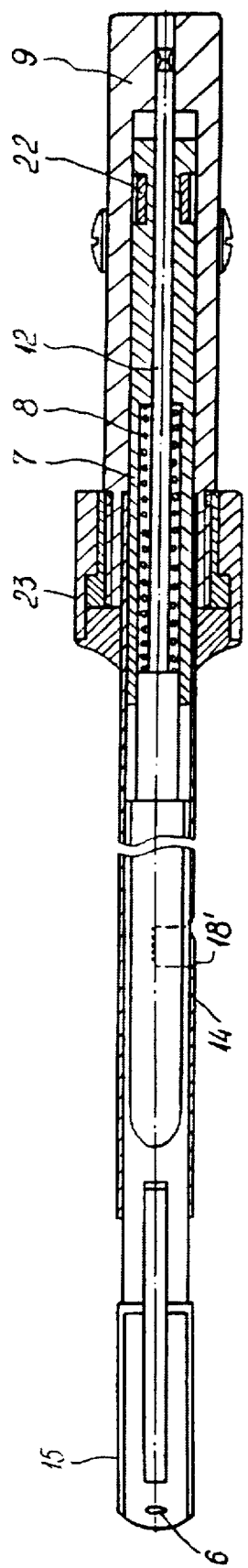
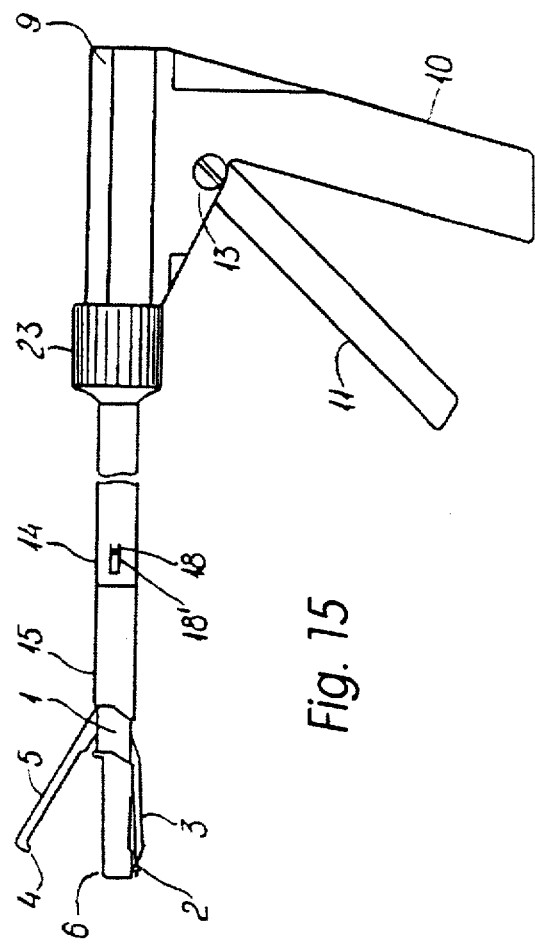
Fig. 14
Fig. 15

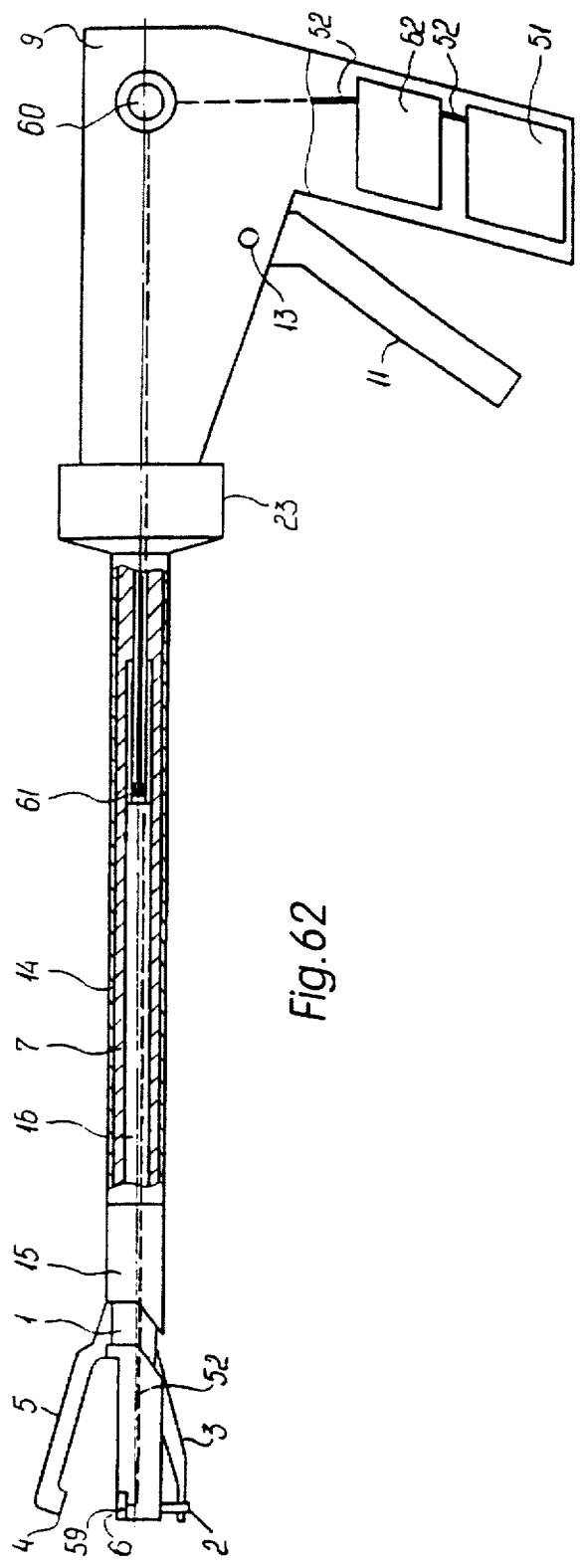
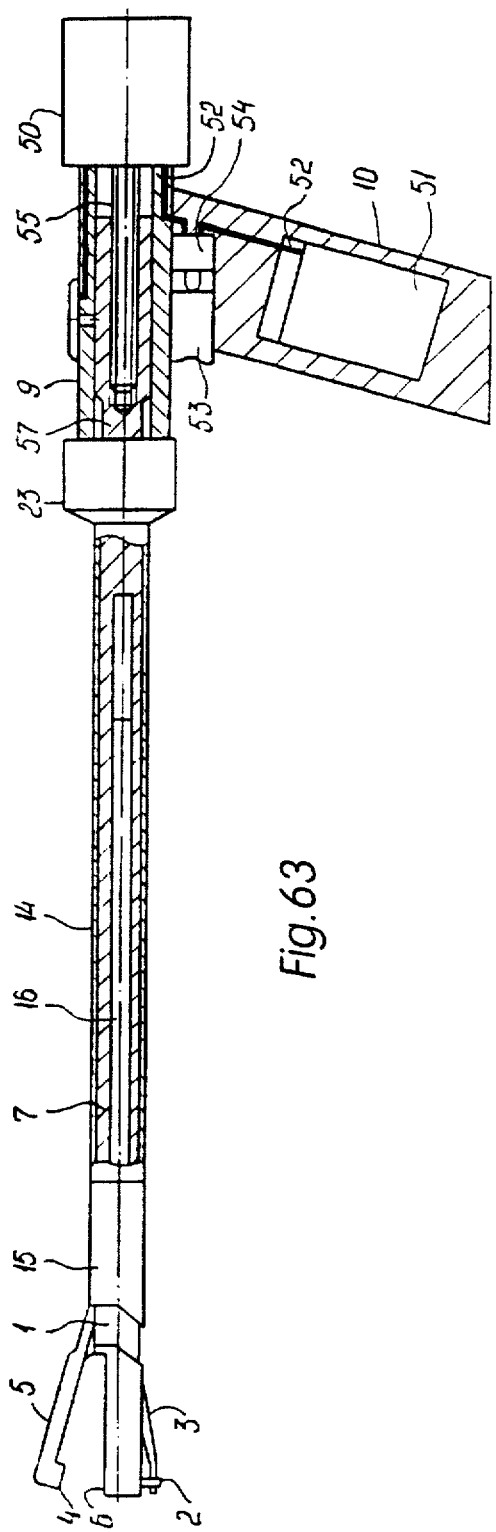
Fig.62
Fig.63

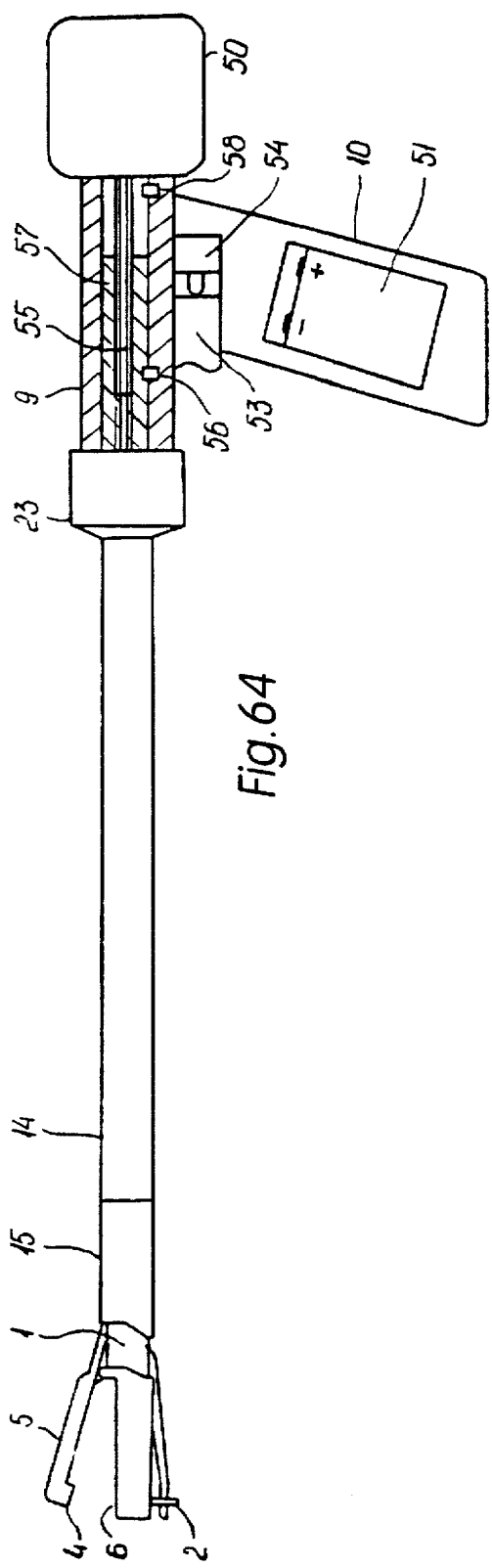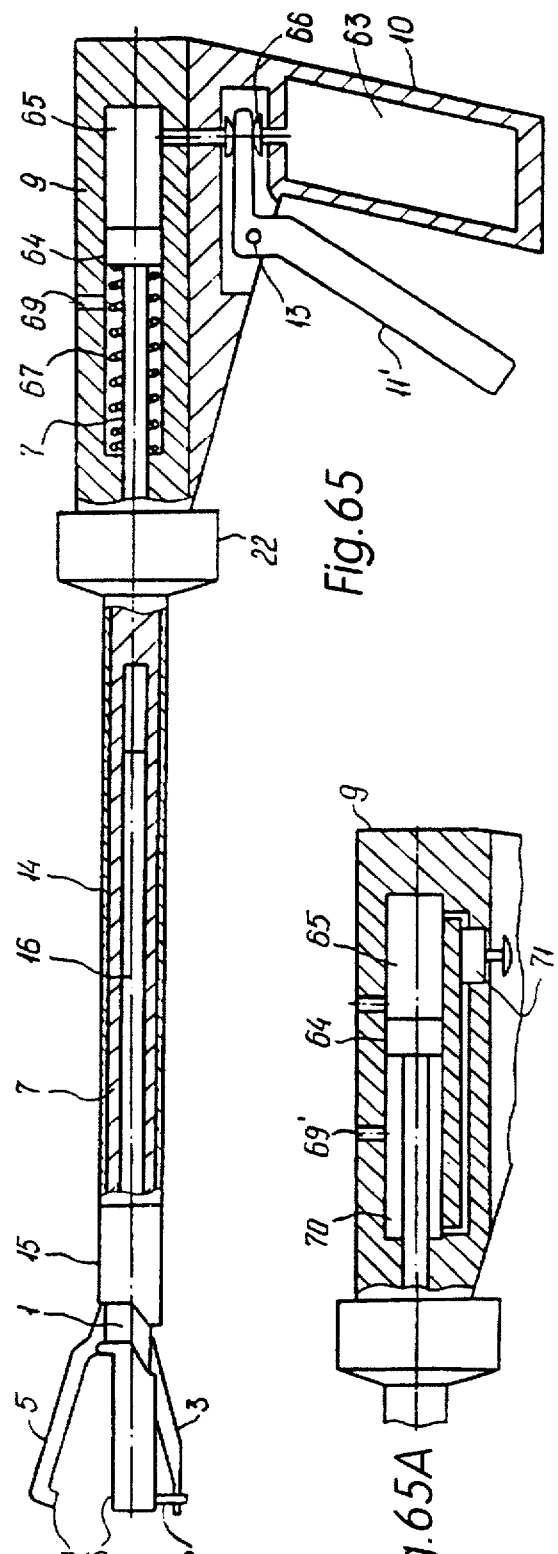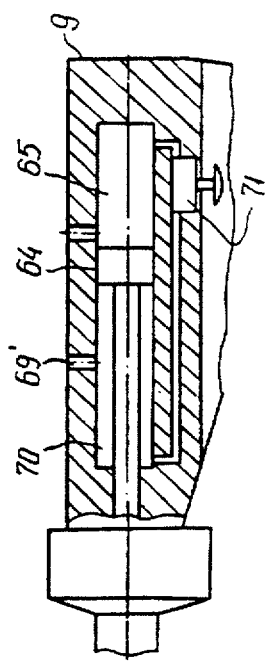

STAPLING DEVICE

This application is a 371 of PCT/US95/00112 filed on Jan. 4, 1995, which is a continuation-in-part of application Ser. No. 08/177,262, filed on Jan. 4, 1994, now abandoned.

FIELD OF THE INVENTION

The present invention relates to a stapling device. More particularly, the stapling device has a unique configuration, suitable for use as a tissue proximation device, an endoscopic surgical microstapler for the attachment of tissues such as for the reanastomosis of gastrointestinal organs and gynecological procedures with "B" shaped staples. The stapler also has an improved feed and insertion mechanism.

BACKGROUND OF THE INVENTION

Surgery often involves the reattachment or reanastomosis of various internal tissues or organs, especially in the later stages of a surgical procedure, e.g. during closure. This tissue fastening may also be a primary object of a surgical procedure, or merely incidental thereto. Presently, there are a number of methods available to perform this tissue proximation and attachment. These include the use of single filament sutures, braided sutures, dissolvable sutures, permanent sutures, steel sutures, staples, clips, dissolvable plastics, permanent plastics, surgical adhesives and other methods. Many of these procedures suffer from the limitations that their applicability is limited, or the procedure is time consuming and requires great skill.

A number of fastener types are available having differing shapes. Each fastener type has properties which determine its applicability, and differing fasteners generally have differing insertion methods and apparatus.

The relevant prior art includes U.S. Pat. No. 3,225,996, GB 1,095,441 and CA 186,605. In addition, United States Surgical Co. has developed various surgical staplers, CMT-0.15 (prior to 1972), CMT-0.25 and CMT-0.4 (prior to 1968, U.S. patent application Ser. No. 108,566) and CMT-3 (prior to 1972, U.S. patent application Ser. No. 312,602, May 22, 1972).

The art has been presented with some difficulties relating to tissue proximation and attachment during endoscopic or laparoscopic procedures. These difficulties may be related to organ manipulation limitations posed by conventional endoscopic instruments. For example, with a dual incision procedure, it is difficult to retain organs in an appropriate and anatomically correct position for the time necessary to complete the attachment. Therefore, endoscopic procedures have evolved in a manner which minimizes the need for extensive organ reattachment or reanastomosis employing the endoscopic instrument. Tools have been made available to perform such procedures quickly and efficiently, but as a result the versatility may be of narrow scope. Procedures which do not fall within the scope of available endoscopic instruments must be performed as full open field surgical procedures. Intestinal reanastomosis may be accomplished by way of intraluminal techniques; however, the available instrumentation tend to be highly specialized for this purpose.

The art also teaches stapling techniques for fastening co-planar sheets, as in the conventional desktop office stapler. The conventional stapler has a number of elements. First, the staple itself is generally a steel wire bent into a U-shape having 90° bends at the corners. The stapler normally includes a sequential feed for a plurality of staples, which are aligned parallel to each other in a feed channel. The channel of staples is fed sequentially to an active region of the stapler by a spring, providing an advancing force from a rear hinged proximal portion toward a distal end, from which the staples are ejected. The hinge connects and maintains in proper alignment, the staple ejection mechanism with a former element (hereinafter a "former") which sits below the tips of the distal-most staple with the staple feed mechanism. When the two hinged portions, the staple ejection mechanism and the former, are pressed together, first the tips of the staple engage the item to be stapled, in alignment with the former. Next, a hammer member having a thickness approximately equal to that of a single staple, presses the staple downward, out of vertical alignment with the channel formed by the supply of staples in reserve, and through the item. As the staple penetrates the item, the tips engage the former and are curved in an inward direction antiparallel toward each other, so that the top of the staple remains substantially straight, while the corners are bent from their 90° configuration to approximately 180° angle with the top portion, with a gentle curvature, in a "B" shape. If the item is thick, then the prongs of the staple penetrate substantially parallel with each other, and the penetrating portions are curved after penetrating the item. The office stapler thus has two phases of operation: first, the two hinged portions move toward each other to surround the item; second, the staple is ejected and penetrates the item to be fastened and the ends bent inward toward each other. These movements are controlled by a first spring force between the hinged portion between the staple feed mechanism and the former, and a second spring force, greater than the first spring force, between the pushing element and the staple feed mechanism. Because of the characteristics of the steel wire, the focussed bending caused by the action of the former causes a plastic deformation. Thus, the staple retains its bent shape after the former is removed. The staple also has elasticity, allowing some play and flexibility of the item after stapling. A "B" shaped staple, because of the elastic recoil of the bent legs, has self adjusting properties. The staple is confined in the active region of the stapler by the adjacent staple on one side and a wall on the other. The staple is generally held in vertical alignment with the adjacent staple by an adhesive which binds the channel formed by the staples. The pusher, generally having the thickness of a single staple, pushes the staple which sits in the active region, shearing the adhesive, and the staple moves downward through a gap. This arrangement is subject to jamming from various causes. For example, two staples may enter the active region simultaneously, or the steel wire may be sheared by the pusher.

It is also known to form an office stapler using, instead of a channel shaped series of staples, a feed wire, which forms staples in situ. The fastener element feed of this type of stapler is somewhat different from the previously described type. The wire is fed from a coil, and is fed to lie substantially parallel to the plane of the objects to be fastened, extending over a form. As the mechanism is activated, the wire is cut to length, and bent over a rectangular form, to form as an intermediate stage a "U" shaped staple. The form is removed from the path of the staple, and the tips are projected toward the former, and deformed thereby after penetrating the objects to be fastened. These wire-form staplers may use a brass wire, supplied from a coil, instead of a steel wire. In a wire-fed stapler, the length of the staple legs may be adjusted between fastenings by determining the length of the cut wire and its positioning during the process.

Surgical staplers are also known for the closure of skin incisions. These staplers differ from office staplers in that they operate without a former portion analogous to that described above. The staple consists of a bent piece of steel having inwardly radially curved downward member with a straight top connecting member. The connecting member is bent in the middle prior to insertion. For application, the tissues are proximated, with the skin edges slightly everted, and the stapling device placed above the incision. The staple is then un-bent to straighten the top connecting member, causing the radially curved portions to penetrate the tissue and hold the tissues in place. These incision closure staples are intended to be removed by a special device which bends the staple in the middle to disengage the downward projecting legs. This type of staple is especially useful for skin closure of abdominal incisions. Various other types of fasteners, including "V" shaped, box shaped, and clips are also available.

Instrument sets are available to perform intestinal resections and reanastomoses. These instruments may use specially designed tissue connection devices. These instruments must, however, be specially designed for a given procedure and the procedure must be performed closely following the standard for that instrument, or rather, the instrument defines a portion of the procedure, and may only be used if the patient meets certain criteria for application of the device. These devices apply a fastening element array in a single action and thus cannot necessarily apply an optimal or controlled traction of the tissues for each fastening element or portion of the closure. Thus, the tissue between the fastening elements may be damaged or suboptimally fixed by the fastening, with the possibility of increased hemorrhaging or tissue necrosis.

SUMMARY OF THE INVENTION

The present invention includes a staple insertion mechanism and method of use thereof which applies surgical titanium wire staples to fasten tissues. The instrument carries a plurality of staples, which are sequentially inserted, and has an 11 mm diameter shaft adapted for endoscopic use through a trochar sleeve. The instrument operates by transmitting a mechanical force from an actuator, through elements in the shaft, to a stapling device in a head portion of the device. The action initially causes a closure of elements which position the tissue to be joined between the staple and the former. In a second phase of operation, further action causes the staple to be advanced through the tissue and causes the ends to be bent by the former to fasten the tissues. In a preferred embodiment, a sliding cylindrical sleeve effects the first and second phase of operations.

The preferred configuration of the stapler has an elongated shaft with an 11 mm outer diameter, for insertion in a standard 10–11 mm ID trochar sleeve. Standard trochar sleeves include sealing elements, e.g. rubber O-rings, for sealing against gas leakage from the body cavity when an appropriate device is inserted in the sleeve or when it is removed. The cylindrical construction of the elongated member of the device allows sealing against the O-rings, preventing the release of gas from, for example, an inflated abdominal cavity, by providing close tolerances between the outer surface of the stapler and the inner surface of the trochar sleeve. The stapler itself prevents substantial passage of gasses or liquids internally. If the trochar sleeve does not include such an O-ring, an appropriate sealing device may be included in the stapler. The construction also allows free rotation and variable length of insertion of the stapler within the trochar sleeve, and rotation of the stapling head with respect to the handle mechanism. The characteristics of the abdominal wall allow for free angular movement in space of the stapler tip, within the trochar sleeve, to allow access to a large portion of the abdominal cavity. Of course, the present stapler is not limited to abdominal procedures, and may be used i in thoracic, retroperitoneal, plastic surgery and other types of surgery. Thus, the tip of the stapler may be positioned within the abdominal cavity with four degrees of freedom, approximating a polar coordinate system with an additional angle of the stapler within the trochar sleeve. In another embodiment, the stapler tip may be articulated, providing further degrees of freedom.

The preferred embodiment of the present invention, the stapler contains a staple cartridge, which may hold between 1 and 200 staples, more preferably between 10 and 50 staples, and most preferably 20 staples. These magazines are preferably interchangeable, and an appropriate quantity of staples in a staple magazine may be selected by the surgeon immediately prior to use. Cartridges are preferably intended for a single use, e.g., for use during a single surgical procedure, after which the cartridge is disposed, and a new sterile cartridge is placed for the next patient. The cartridge includes the staple feed mechanism as well as the pusher and former. The handle, trigger and actuation portions may be reusable, but it is preferred that these portions also be disposable. The staple cartridge may also be an integral portion of a disposable device.

The stapler, due in part to the length of the arm holding the former member and its clearance from the core portion of the magazine, can attach tissues having a range of thicknesses. For example, a preferred embodiment of the stapler according to the present invention can accommodate tissues in excess of a total of about 4.0 mm in combined thickness tissues for attachment, so long as the tissues may be compressed to about 2.5 mm, the clearance between the former arm and the body of the stapler, without permanent damage to the stapling mechanism, or substantial unintended tissue damage. The minimum tissue thickness is preferably about 0.5 mm. Thinner tissues tend to be more fragile and may be damaged by the staple and stapling mechanism. In addition, very thin tissues often do not require a sturdy proximation device and a delicate technique is preferred. For tissue thicknesses in excess of about 3.0 mm, a larger stapler is preferably employed, which has increased clearances and employs larger staples. Thus, the stapler according to the preferred embodiment of Example 1 is designed to accommodate a range of tissue thickness, and may be modified according to the present design principles to perform a wide range of surgical procedures. The present stapling process possesses a significant tolerance, such that the tissue thickness may vary from about 0.5–2.5 mm, compressed tissue thickness, which corresponds to a greater thickness range, up to about 4 mm thickness uncompressed, depending on the organ.

The staple according to the preferred embodiment, is formed from a surgical titanium wire, the preferable staple having a width of 3 mm (the top bridging portion), a height of 4 mm (the length of the leg) and a wire diameter of 0.2 mm. The preferred titanium alloy wire for fabrication of the staples is 40KXHM. The staples may be formed in a standard manner, by bending a wire over a form having broken sharp edges, with an angle of about 90°, which rebound to an angle of slightly greater than 90°. In the preferred embodiment, the legs are bent, after forming, to about 105° from the horizontal (the top bridging portion). In the preferred embodiment, the wire diameter for the staples may vary from 0.15–0.2 mm, without modification of the design. Staples smaller than about 0.15 mm or larger than about 0.2 mm require modifications to the design of the stapler, especially the staple feed and insertion mechanism.

The surgical stapler consists of two major assemblies: first, a handle with a tube like body, having a trigger element connected to an actuation linkage. The second element is a magazine filled with a plurality of staples, a pushing element for extracting staples from the stapler and pushing them towards a former. The staple magazine is preferably detachable and interchangeable, allowing multiple uses of the handle assembly with a disposable or interchangeable staple cartridge, which is attached to the tube-like body of the handle through a coaxial linkage with a spring loaded catch. Because of the medical application of this device, the staple magazine has been designed for a single use, thus reducing the problem of ensuring sterility and eliminating staple jams. As stated above, a fully disposable design may include an integral staple cartridge.

The handle of the stapler is preferably ergonomically adapted for manual use by a surgeon, in order to enhance the functional usefulness of the device and to reduce the probability of error. The trigger, dependent from the handle, is also ergonomically adapted for depression by the surgeon with his index finger, or combination of index and middle finger. The depression force of the trigger should thus be great enough to prevent accidental activation of the device, yet low enough to allow repeated stapling operations without strain or cramping of the surgeon's hand. The mechanism is designed so that an initial depression of the trigger with respect to the handle causes a movement of elements of a mechanical linkage, which acts to hold the tissue in place and subsequent depression causes insertion of the staple by advancing the staple legs through the tissue, so that the legs are bent by the former after penetrating the tissue.

In various embodiments according to the present invention, the trigger may be passively linked to the stapling head, wherein all of the forces and power necessary for stapler operation are derived from the trigger. The trigger may also be linked to control a power source in an actively assisted system. In such instance, the trigger depression provides only a part or none of the stapling operational power. It is preferred that the trigger be provided with a means for providing a force feedback from the stapling head to the surgeon's hand. This allows force feedback to the surgeon's hand, which enhances the feel of the device, and provides greater safety due to better control by the surgeon. This force feedback may be a mechanism directly linked to the stapling head, or a synthesized force based on a sensor and feedback actuator.

The staple magazine has a channel with an approximately "U"-shape. An inner portion inside an outer portion defines a trapezoidal "U" shape with the tips of the "U"-shape closer together than the length of the top bridging portion. The staple magazine is charged by elastically compressing the legs of the "U"-shaped fasteners together to approximate the trapezoidal shape of the channel, to provide clearance for insertion of the staple into the channel. Thus, with the end plate removed, staples are sequentially inserted into the shape-conformed cavity, with care being taken to hold previously inserted staples in place while a next staple is inserted. The first staple inserted presses against a trapezoidal shaped form linked to a feed spring, and which transmits the spring force. The spring force is likewise transmitted through any staples in the channel to the staple adjacent to the active staple (the last staple inserted), which, in turn, is pressed against an end plate. Of course, other staple insertion methods are possible, which will result in a similar final configuration.

Thus, when inserted in the channel-like cavity, the staples have but a single degree of freedom, advancing along a horizontal or longitudinal axis of the stapler due to the staple feed spring. The active staple has an additional degree of freedom. In addition to having an axis of movement along the longitudinal axis of the stapler, constrained by the end plate, it also has a movement along the vertical axis of the stapling head, which is defined by a recess in the end plate, the pusher, and a lower aperture. The active staple is prevented from falling out of the lower aperture by the frictional forces (e.g. it is force locked) of the adjacent staple, pressed against it by the spring force, and the walls of the recess of the end plate. If necessary, the active staple may also be held in place by a form lock system, having a mechanical linkage which releases the staple as the pusher begins advancing toward the former.

The stapler may also include a plurality of staple channels, for sequential insertion of a plurality of staples. In this configuration, the staples may advance along parallel or antiparallel paths, with a former having a plurality of forming surfaces. For example, six staples may be simultaneously inserted in a staggered double row in a single operation, in so-called "chess" fashion. The stapler includes three parallel feeds from one side, and an additional three parallel feeds, staggered from the first feeds, from the other side. These staples will, in this configuration, generally feed perpendicular to the longitudinal axis of the stapler shaft.

The pusher system may also be formed differently in order to reduce the maximum diameter of the device. For example, a pair of sector gears, pivoting lateral to the staple channel, may be employed to eject the staple. A linear pusher may also be displaced by small gears lateral to the staple channel.

The optimal angle of bending of the legs of the staple while in the trapezoidal feed is determined by the material of the staple and its configuration. This angle should be such that the tips of the staple adjacent to the active staple are medial to the tips of the active staple by at least the diameter of the wire from which the staple is formed. The gap formed by the first recess is preferably slightly deeper than the gauge of a single staple to provide clearance, but substantially smaller than the combined width of two staples. The maximum deformation is limited by the elastic deformation limits of the staple, however. If the staple is bent too far, then it will be difficult to release the staple from the feed into the active position, due to a too great frictional force and the possibility of plastic deformation of the staple thereby preventing expansion to a perpendicular state. Because the staple is retained in the feed initially by the presence of the active staple, and then by the pushing element, when the pushing element is returning to its resting position above the staple, the tips of the adjacent staple will be forced by both the feed spring and the differential release of tension on the tips as compared to the top bridging portion. Thus, the adjacent staple undergoes a complex, dynamic-angular movement into the active position, which further helps to accurately position the active staple and prevent interference from the new adjacent staple.

The trapezoidal shape may be constant over the length of the feed channel, or be tapered. If tapered, it is preferable that the feed channel taper inwardly.

A catch or lock mechanism may be provided to prevent advance of a staple, so that the stapler may be inserted and removed from the trochar sleeve without undesired ejection of staples. This catch or lock may be manually engaged, or automatically engaged by the presence, absence or transition of the trochar sleeve. Alternatively, the staples may be placed in the feed channel alternating with dummy staples which are formed of a biocompatible or dissolvable composition. Therefore, the stapler may be removed between each staple insertion. If the pusher arm is eliminated and replaced with a different type of ejection system, such a catch or lock, or alternating staple system may be avoided.

The staples may be automatically inserted in the magazine, eliminating the need for manual insertion and the concomitant problems of ensuring cleanliness and sterility. Otherwise, the staples may be manually inserted into the guide channel of the staple magazine. For insertion, a biocompatible adhesive may be employed to adhere a plurality of staples in parallel, so that they may be loaded together. This adhesive may then be removed, such as by a solvent, to leave the staples in their free, independent state.

When the pusher advances downward along the stapling head vertical axis, it sits in a second, deeper recess in the end plate, and initially contacts the top bridging portion of the staple, that part which bridges the two legs. The second recess is deeper and narrower than the first recess, and the lateral walls have a tight clearance to the pusher. The depth of the second recess is such that it protrudes about one staple width into the first recess, so that only a single staple resting against the end plate will be vertically displaced, and any adjacent staple will not be disturbed. Thus, the pusher in the second recess is flush with the inner face of the end cap. As the pusher advances vertically downward, the sharpened points of the legs of the staple emerge from the lower aperture of the stapling head, aligned with the vertical axis thereof.

When the operator presses the trigger, the bottom surface of the pusher element contacts the top of the active staple in the magazine. The active staple is seated in a recess in the end cap, which guides the staple vertically. The pusher is seated in a deeper recess in the end cap, so that the pusher may have a width greater than the width of the staple. The pusher does not advance the staple adjacent to the active staple because the width of the pusher is carefully controlled to be equal to the depth of the recess plus the width of the active staple. The staple tips are forced into the tissue matrix located between the staple tips and the former, and begins to penetrate.

In operation, the tissues to be attached lie in parallel planes immediately below the advancing staple and between the lower aperture and the former. The tips of the staple thus pierce the first tissue, emerge from the first tissue and pierce the second tissue. The tips of the staple, upon emerging from the second tissue, are in contact with the former. The tips of the legs of the staple follow a curvelinear path defined by the former, and curve upward, preferably again passing through the layers of tissue, depending on the thickness of the tissue and length of the staple legs. The tips may extend beyond the top bridging portion, and for this reason a gap is formed in the central portion of the pusher to provide adequate clearance for the staple tips as they are directed upward. After the former is released, the bent staple legs may rebound, and in fact the "B" shape allows a self adjustment of the staple to the tissue thickness. If desired, the former may be displaced a desired distance from the staple ejection port, to allow control over the location of the staple tips after forming. The former displacement may be adjustable between stapling operations.

The former is a hard steel element having a pair of somewhat ellipsoidally curved indentations, which are aligned adjacent, with their long axes parallel to each other. The indentations are configured to have a curvature having a radius smaller than the desired final configuration, so that it rebounds to the desired shape due to elasticity of the staple wire. The indentations preferably have a gradually decreasing radius of curvature toward the center of the former. The angle of the indentation with respect to horizontal is about 20° at the lateral aspect, and about 45° at the medial aspect along the centerline of the indentation. The walls of the indentations are each formed of five substantially planar faces, a horizontal lower face, two canted walls, on either side of the horizontal lower face, which are inclined about 45° from vertical, having planes which intersect below the indentation, and two upper walls which are parallel and are about 7° from vertical, having an intersection below the indentation, thus forming a piecewise approximately concave configuration of the indentation, when viewed in cross section.

The optimal staple configuration, after forming in the stapler, is a somewhat rectangular shape, with a straight top bridging portion, having relatively sharp square bend at the corners, formed in the original production of the "U"-shaped staple, with the legs curved semicircularly up toward the center of the top bridging portion. The tips of the leg preferably extend to about the position of the top bridging portion, making a second pass through the tissues in the central region, but may extend to a point before or after intersecting the top bridging portion. As stated above, the position of the tips may be controlled by adjusting the position of the former during stapling. The legs have a gentler curvature toward their ends than at the preformed corners.

It should be noted that, biologically speaking, tissues having a large connective tissue or muscular wall width tend to be subjected to greater forces than those with thinner walls. Thus, the proximation of thick-walled organs preferably should be performed with a larger gauge wire staple, with a greater length between the legs in order to achieve maximum strength and most efficient closure. Long-legged thin wire gauge wire staples tend to have their tips wander off their optimal path during insertion, so that care should be taken in selecting the staple for use in procedures involving particularly thick, dense or muscular organs.

The gauge of the staple wire is determined by the geometry of the staple, the material characteristics, and the intended application. Of course, the stapler must be designed for a particular staple or staple size, and therefore the selection of a stapler limits the choice of staples which may be used. In a preferred embodiment, a 0.2 mm diameter titanium wire is used. The tissues to be proximated are usually intestine, but may be other tissues, including stomach, esophagus, reproductive organs, muscle, fascia, omentum, lung, bile duct, renal pelvis, ureters, bladder, blood vessels, etc. For, e.g., the reanastomosis of ileum, where the lumen wall has a width of about 2 mm, a surgical titanium staple having legs 4 mm long and 0.2 mm diameter is preferred. While the free tissues have a thickness together of 4 mm, the staple is primarily intended to join the adventitia layers, and may compress the other tissue layers, which will overgrow the staple in healing. Thus, in healing, the staple may be embedded in the tissue. For stapling parts of the stomach subject to great stresses, it is preferred that a larger staple having greater strength is used. This is because portions of the stomach are muscular, having a thick muscular layer, and may be subject to almost continuous and powerful contractions.

By the present principles, the stapler according to the present invention could be scaled to specifically accommodate general gastric surgery; however, tests have been conducted with good results using the stapler according to the present invention for a posterior pyloric-duodenal anastomosis.

The elongated body of the stapler consists of an inner core, slidable with respect to an outer concentric sleeve. The sleeve terminates in a pair of cam-like shaped edges, a top edge and a bottom edge. The top edge is aligned with the pusher arm, while the bottom edge is aligned with the former arm. The pusher arm has a return spring and is linked to the pusher, such that a depression of the pusher arm toward the core causes the pusher to advance downward along the vertical axis in the second recess of the end cap, between the end cap and the staple feed channel. The former arm also has a spring return and terminates in the former. When depressed toward the core, the former aligns with the path of the staple tips. The sleeve edges are so shaped that, with the core of the staple magazine holding the pivot points of the arms in fixed relation, and therefore displaceable along the longitudinal axis with respect to the outer sleeve, the former arm is pressed by the relatively advancing edge of the outer sleeve toward the core before the pusher arm advances the pusher to advance the staple downward. This sequence is determined by the shape of the surface of the pusher arm, the shape of the surface of the former arm and the shape of the top and bottom edges of the sleeve. The pusher arm has three portions of its surface, a first portion with a narrow angle with respect to the longitudinal axis, a short second portion, distal to the first portion which has a steep angle, and a third portion, distal to both the fist and second portions, which has an narrow angle. Thus, the advance of the outer sleeve over first portion of the pusher arm causes little depression of the pusher arm, the advance of the outer sleeve over the second portion with a steep angle causes a rapid depression of the pusher arm midway through the stroke to push the staple down into the former to deform the staple into its final configuration, and the further advance of the outer sleeve over the pusher arm has little effect, but provides assurance that the stapling cycle is completed and the staple properly fastened. In contrast, the former arm has essentially a single, mild angle with respect to the longitudinal axis, and the former thus advances toward the staple and is completely in position prior to initial depression of the pusher arm. The return spring of the former arm has a low spring tension, while the spring tension for return of the pusher arm is high.

Because of the relatively high force exerted by the sleeve against the axially moving spring loaded arms, the relatively thin sleeve should be formed of a tough material. The base of each of the arms preferably have a smooth surface finish, in order to reduce the wear on the sleeve due to surface irregularities. In a reusable stapler configuration, the arm material should be softer than the sleeve, as any wear of the arm base will be more distributed and less troublesome than wear of the sleeve edge. These conditions may be determined, for example, by using a cold-rolled steel sleeve and cast arms.

While the preferred embodiment represents a direct mechanical linkage between the handle/trigger mechanism, other sources of power are possible. These power sources include electrical, hydraulic, pneumatic, stored mechanical energy, as well as, in certain circumstances, stored chemical and explosive chemical energy. Initially, it is noted that the power source may be stored in the handle, a simple proposition due to the fact that less than 200, and preferably only 20 to 50 staples need by inserted. Otherwise, the energy source may be external to the stapler, and electrical, hydraulic, pneumatic or mechanical energy transmitted to the stapler through a tether cord.

Any form of stored energy may reside in or near the handle, and be transduced into mechanical energy in the handle portion, and therefore the remainder of the operational details are essentially identical to the stapling system of the aforementioned preferred embodiment. Alternatively, the transducer may reside closer to the stapling head, in the elongated member or in the head itself. Further, the transducer system may form a functional part of the stapling system, and replace or modify various mechanical features of the above described preferred embodiment.

An electrically operated embodiment according to the present invention employs an electrical power source located in the handle to provide power to an electromechanical transducer. The power source may be, e.g., a primary battery or a rechargeable battery. The handle of the stapler has, mounted at the front portion thereof, and extending downward, an electrical switch. The switch preferably has a safety interlock which prevents accidental activation of the stapler during use.

A first electrically powered embodiment makes use of a motor, which drives a helical screw gear, causing a linear movement of a follower. The follower is linked to an assembly which causes closure of the stapling head. Completion of a stapling operation is detected by a limit switch, which initiates a reversal of the motor, bringing the system to the starting position, which may be detected by a second limit switch. Thus, the closing and opening action are automatically determined.

Alternatively, the helical element may be dual-cut, to provide automatic return without need for reversing the motor. This arrangement further eliminates the need for one of the limit switches, particularly the one which detects maximum excursion. Further, since the return stroke requires less torque than the excursion/stapling stroke, the return may be faster, e.g. a steeper helix, than the stapling stroke.

A second electrically powered embodiment may be constructed using a solenoid driven actuator. The solenoid may be a linear-acting unit located in the base of the elongated member, operated to longitudinally displace the core with respect to the sleeve. A plurality of solenoid actuators may also be employed to individually control the pusher and former, and possibly accessories of the device.

In an pneumatic embodiment according to the present invention, the motive force for the stapling mechanism is provided by a source of compressed air. The source can be a compressed gas cylinder contained in the handle, an internal pump, or an external source fed by a tube from outside the device. The compressed gas is used to move a piston in a cylinder, which, in turn, actuates the stapling mechanism. The piston may be located in the handle or near the stapling cartridge. The trigger actuates a valve, which vents gas into the cylinder, moving the piston. The return stroke can either be implemented by a spring, acting against the piston, or by use of a double acting cylinder. In either case, the gas must vent from the cylinder at the completion of the stroke. In a double acting cylinder embodiment, the gas moves the cylinder forward, until a valve opens at the end of the stroke. The valve vents the gas. Simultaneously, the outer cylinder is connected to the compressed gas, wherein it returns to the starting position, and the gas vents. The gas may vent to the atmosphere near the cylinder, or be shunted away.

The force for driving the stapling mechanism may also be hydraulic. The source of power for this hydraulic system may be a trigger mounted pump, which incidentally may also be analogously used for a pneumatic-pump based system. Alternatively, the system may have an external source of hydraulic power. Because hydraulic fluid is incompressible, the use of a hydraulic systems also allows miniature hydraulic actuators to be incorporated in the stapling head. These miniature cylinders may be separately actuated and controlled, giving fine control over the operation of the stapler and any associated devices. Hydraulic fluid must be contained in a closed system, and should not be vented, unless a physiologic solution is used.

The stapler of the present invention may advantageously be adapted to include tissue forceps, for holding the two layers of tissues to be joined in place and under appropriate tension for the stapling operation. These forceps would consist of one or two active forceps systems, for holding the tissue layers either individually or together, at points on either side of the stapling head. Advantageously, these forceps systems would be individually controlled by cables, rods, cylinders or solenoids and would lock closed when the tissues are in place, to be unlocked selectively after stapling. This forceps system should have, in addition to the closing action, at least one axis of movement so that the tension on the tissue may be controlled. Because the stapling mechanism is normally used sequentially, it is advantageous if the forceps mechanism provides for an advancing of the stapling head without a requirement for unlocking and repositioning of the stapling head. This may be provided, for example, by allowing movement of the forceps mechanism with respect to the stapling head with tissue locked in place.

The forceps included with the stapling mechanism may also be used for other purposes in the surgical procedure. Likewise, the present stapling mechanism may be combined with other known endoscopic instruments in a single apparatus having enhanced functionality. These instruments include cameras, illuminators, forceps, biopsy tools, cautery, clip applicators, laser surgical tools, etc. Optical elements may be located with an optical axis longitudinally oriented at the tip of the device, or positioned to be used to illuminate or view the tissue being stapled.

The present stapling device provides a hinged former. However, the former may also be linked to the core of the device by a multilink articulated mechanism which provides a substantially linear movement between the core and former. Such a mechanism is particularly advantageous with an inserter for variable length staples, such as might be possible with an in situ formation of staples, or a multiple feed mechanism with a plurality of staple sizes. In such instances, the former would be accurately positioned with respect to the staple feed mechanism regardless of the thickness of the tissue, which could be in excess of 5 mm in such an embodiment. When a variable length staple is employed, the travel of the pushing element preferably also adapts to the length of the leg of the staple.

Of course, it should be realized that, while the various embodiments according to the present invention include provision for inserting only one staple at a time, the present invention could also be adapted to perform a tissue proximation by inserting two or more staples simultaneously.

OBJECTS OF THE INVENTION

Therefore, it is an object of the present invention to provide a surgical stapler according to the apparatus of claims 1 to 7 and the method of claims 8 to 10.

It is also an object of the present invention to provide a stapler including (a) a manually operable mechanism producing an actuation signal; (b) an actuation signal transmission system; (c) a staple cartridge, comprising: (i) a staple advancing system for applying an advancing force; (ii) a longitudinal guide, for maintaining a plurality of U-shaped staples parallel to each other along a longitudinal axis; (iii) an end guide, having a vertical axis, said vertical axis being substantially orthogonal to said longitudinal axis, a first recess aligned with said vertical axis and a second recess, deeper than said first recess, aligned with said vertical axis; (iv) a lower aperture, aligned with said vertical axis; and (v) a displaceable staple press, displaceable along said vertical axis in said second recess, and guided thereby, being for displacing a staple along said vertical axis without vertically displacing an adjacent staple; (d) a displaceable former, for plastically deforming staple ends, said former being displaceable between a first position in which the former is substantially displaced along said vertical axis from said end guide and a second position in which the former is substantially proximate to said end guide; and (e) control means for displacing said former from the first position to said second position prior to displacing said staple press toward said former by moving said press arm.

It is a further object of the invention to provide a surgical stapler cartridge, comprising: (a) a staple advancing system for applying an advancing force; (b) a longitudinal guide, for maintaining a plurality of staples parallel to each other along a longitudinal axis, said guide having a horizontal top portion, substantially perpendicular to said vertical axis, and two semi-vertical portions, each having a plane oriented downwardly inward at such an angle which does not cause plastic deformation of a staple inserted in said guide, having an open end wherein said semivertical portions merge with vertical portions having walls which are vertically aligned; and (c) an end guide, having a vertical axis, said vertical axis being substantially orthogonal to said longitudinal axis, a first recess aligned with said vertical axis and a second recess, deeper than said first recess, aligned with said vertical axis; (d) a lower aperture, aligned with said vertical axis; and (e) a displaceable staple press, displaceable along said vertical axis in said second recess, and guided thereby, being for displacing an active staple along said vertical axis without vertically displacing an adjacent staple, said active staple being confined upwardly by said staple press, laterally by walls of said first recess, and rearwardly by said vertical walls of said open end of said longitudinal guide.

A still further object of the present invention is to provide a method of attaching biological tissue, comprising the steps of: (1) providing a stapler having a stapling cartridge, (2) placing the tissues to be attached along the vertical axis of the staple press, between the staple and the former; (3) displacing said former from the first position to said second position in a first phase without substantially displacing said staple press; and (4) displacing said staples press toward said former to displace a staple by moving said press arm in a second phase, after said former is in said second position.

It is a still further object according to the present invention to provide a wire feed stapler, in which a linear wire is cut to length and bent into a "U" shape, prior to insertion in which the staple legs are deformed by a former to fasten the tissue.

The present invention may also include a staple ejection mechanism in which a portion of the mechanism resides lateral to the staple feed channel, to allow a reduced instrument diameter.

BRIEF DESCRIPTION OF THE DRAWINGS

Embodiments of the present invention are shown in the figures in the drawings, in which:

FIG. 12 is a side, partial cutaway view of the stapling portion of a preferred embodiment of the present invention in an open condition;

FIG. 13 is a side, partial cutaway view of the stapling portion of the embodiment of FIG. 12, in a closed condition;

FIG. 14 is a top cross section view along F—F (FIG. 1), G—G (FIG. 12);

FIG. 15 is a side view of a preferred embodiment of the present invention;

FIG. 62 is a partial cutaway side view of staple sensing embodiment according to the present invention;

FIG. 63 is a partial cutaway view of an electrical embodiment according to the present invention;

FIG. 64 is a partial cutaway view of an electrical embodiment according to the present invention;

FIGS. 65 and 65A are partial cutaway views of a pneumatic embodiment according to the present invention;

DETAILED DESCRIPTION OF THE PREFERRED EMBODIMENTS

Example 1

Figure 1:
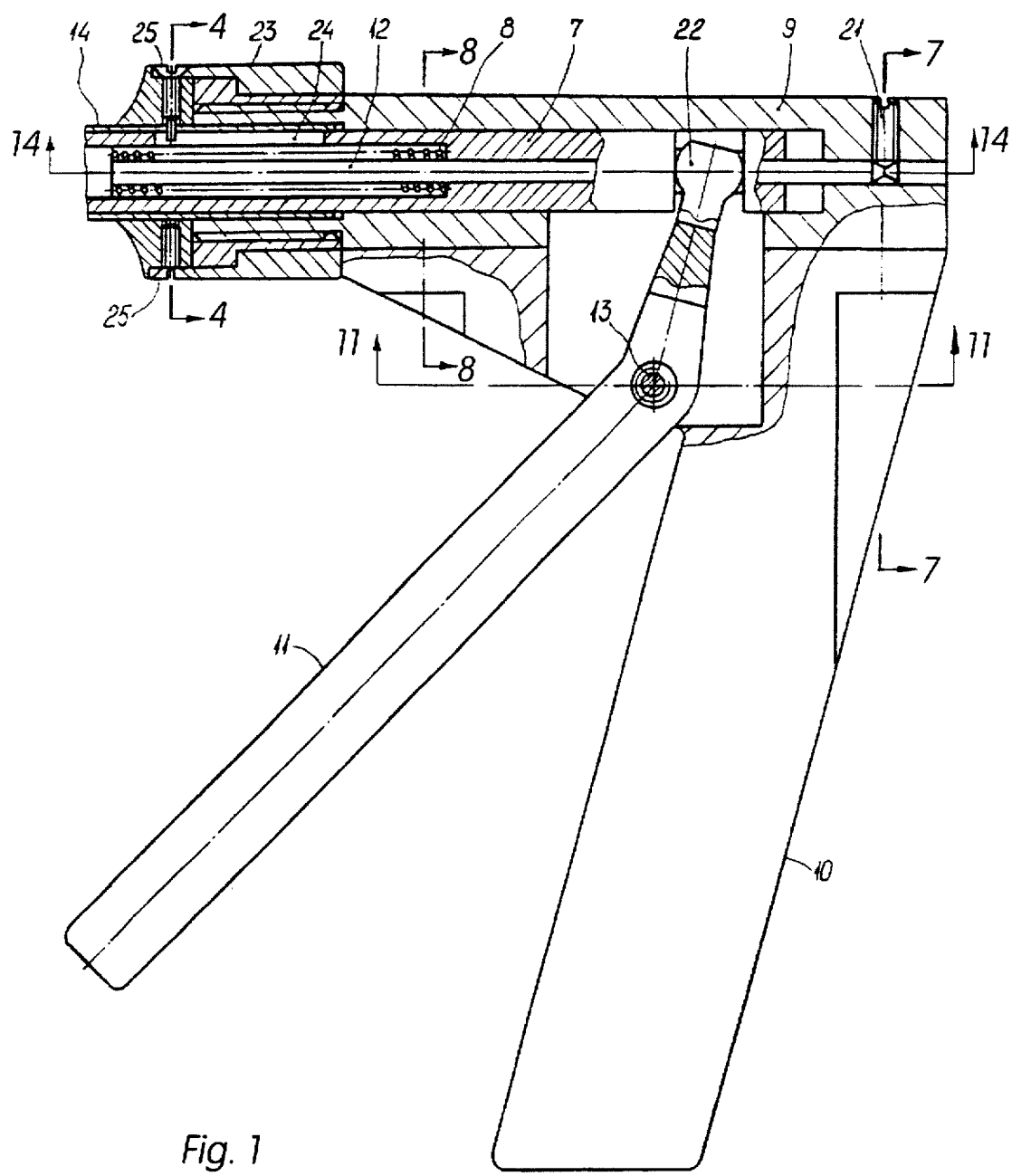
FIG. 1 is a cutaway side view of a handle of a preferred embodiment of the present invention.
Figure 2:
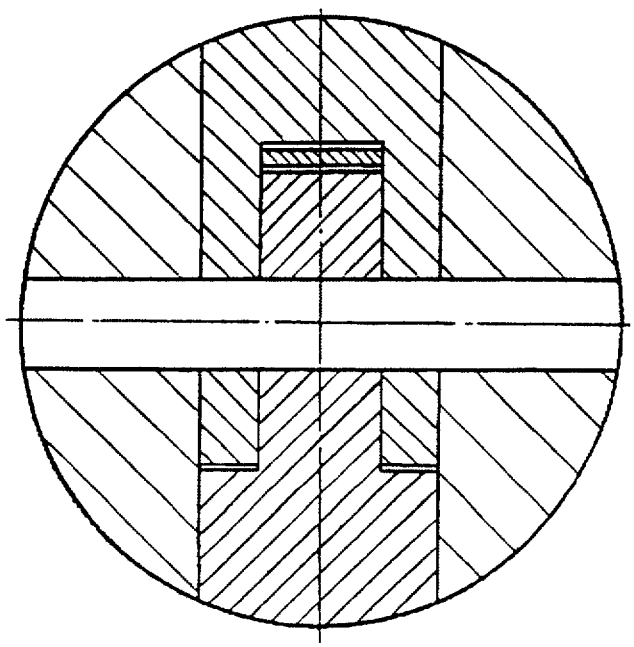
FIG. 2 is a cross section along H—H through a hinge portion of FIG. 16.
Figure 3:
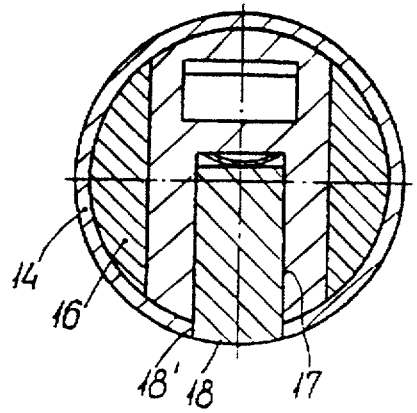
FIG. 3 is a cross section along D—D through a catch portion of FIG. 12.
Figure 4:
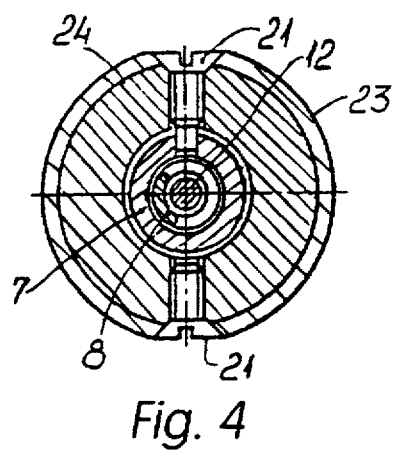
FIG. 4 is a cross section along A—A through a collar portion of FIG. 1.
Figure 5:
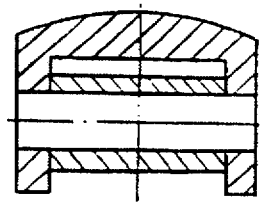
FIG. 5 is a cross section along I—I through a spring portion of FIG. 16.
Figure 6:
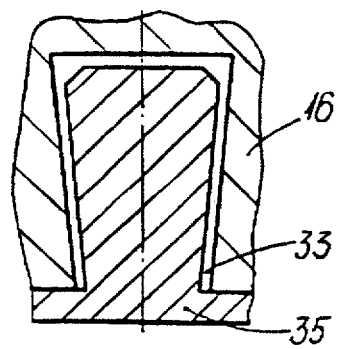
FIG. 6 is a representative cross section through the channel portion of the staple feed mechanism.
Figure 7:
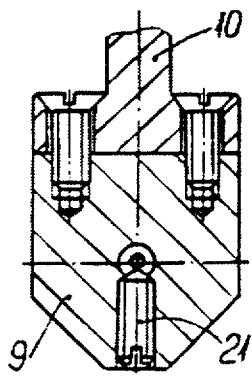
FIG. 7 is a cross section along B—B through a set screw portion of FIG. 1.
Figure 8:
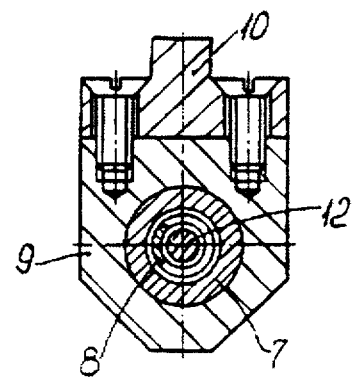
FIG. 8 is a cross section along C—C through the handle body portion of FIG. 1.
Figure 9:
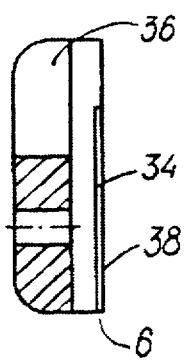
FIG. 9 is a cutaway side view of the end cap along AA—AA of FIG. 10.
Figure 10:
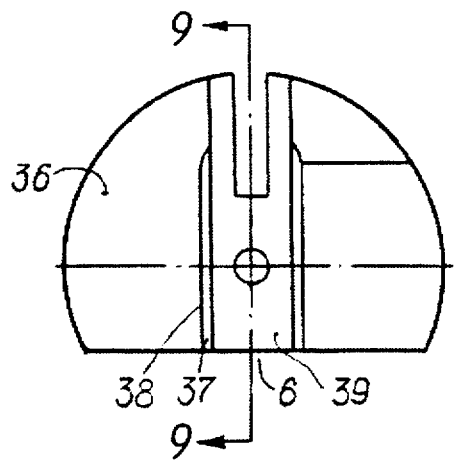
FIG. 10 is a front view of the end cap.
Figure 11:
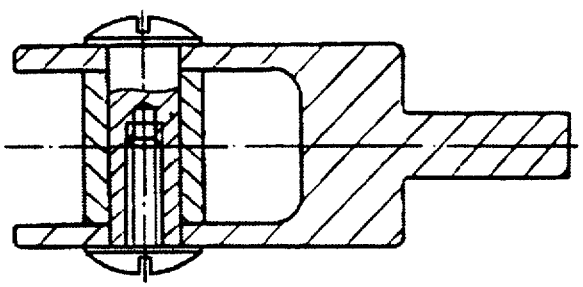
FIG. 11 is a cross section along E—E through a trigger hinge portion of FIG. 1.
Figure 16:
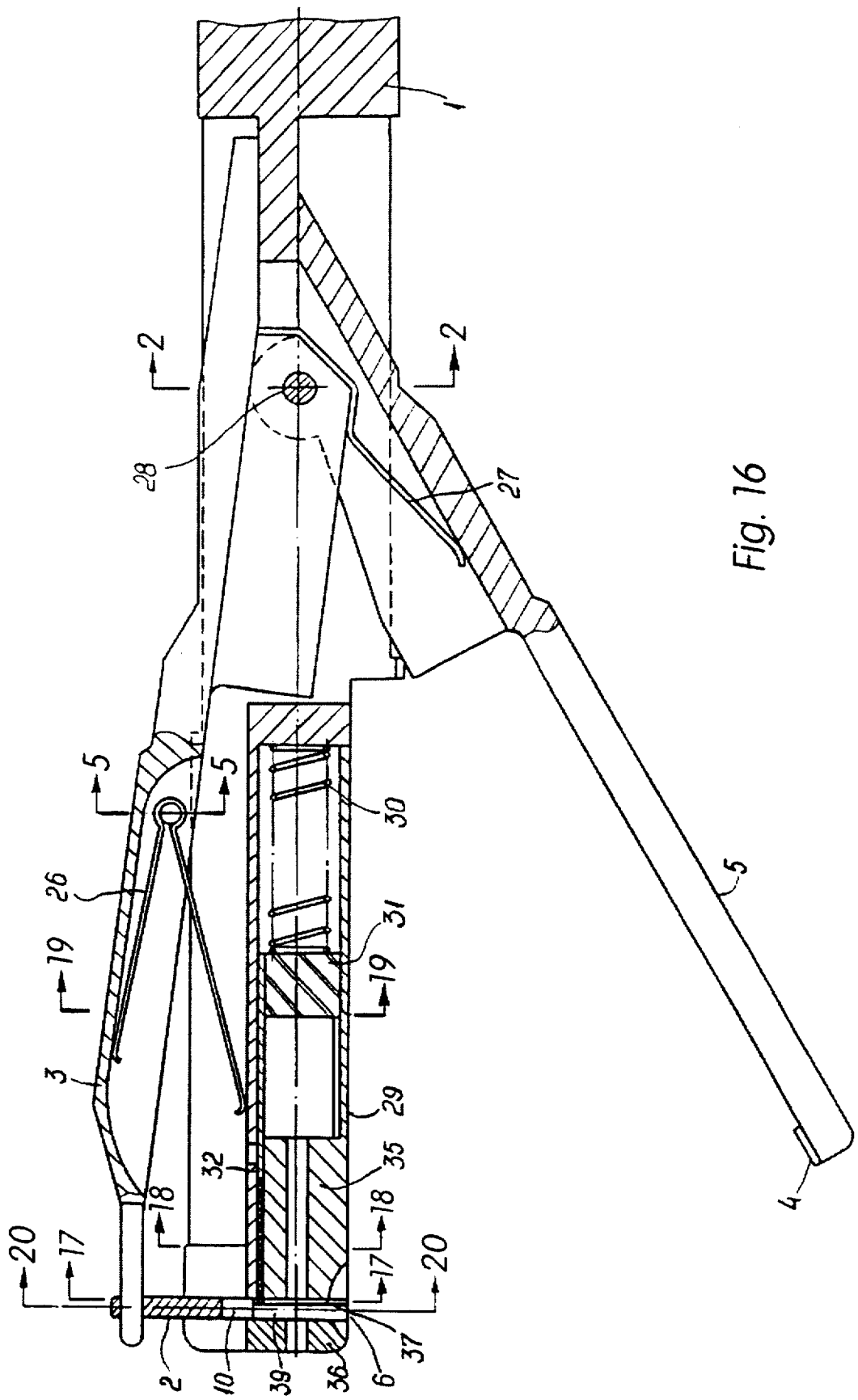
FIG. 16 is a side cross section view of the staple magazine assembly according to the present invention.
Figure 17:
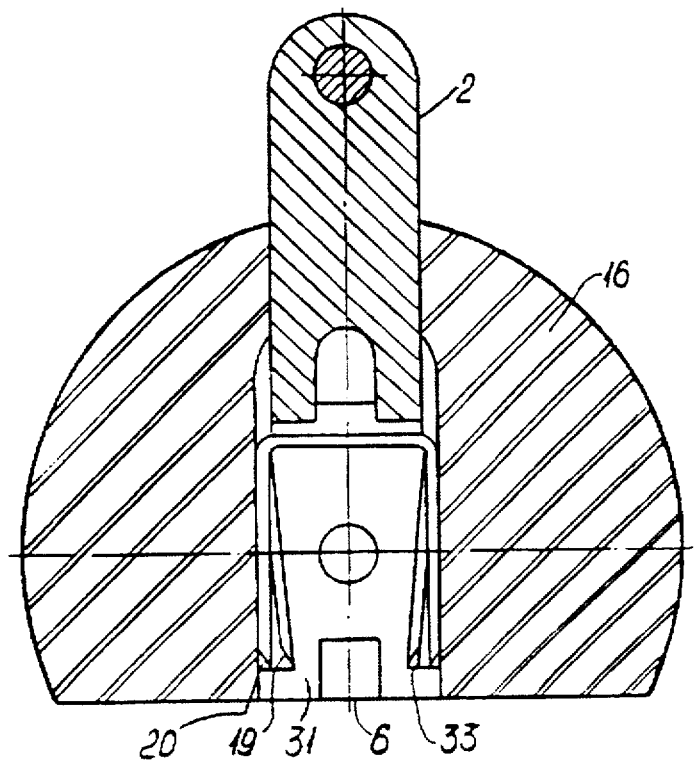
FIG. 17 is a cross section along L—L through a pusher mechanism of FIG. 16.
Figure 18:
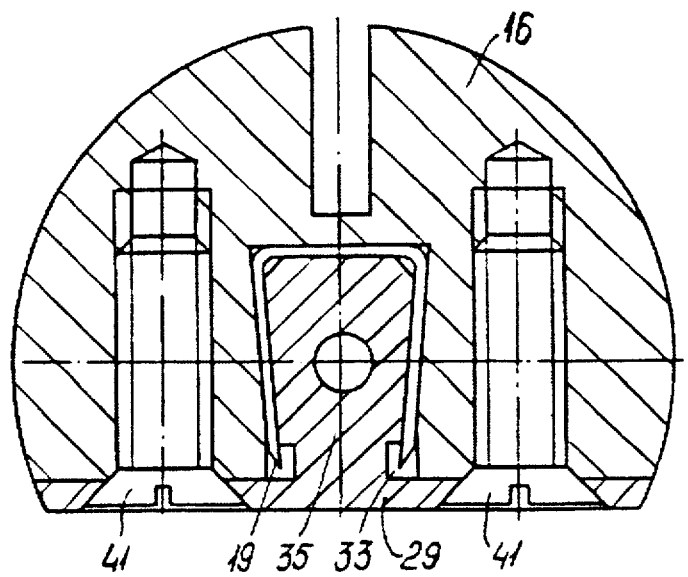
FIG. 18 is a cross section along K—K through a staple channel of FIG. 16.
Figure 19:
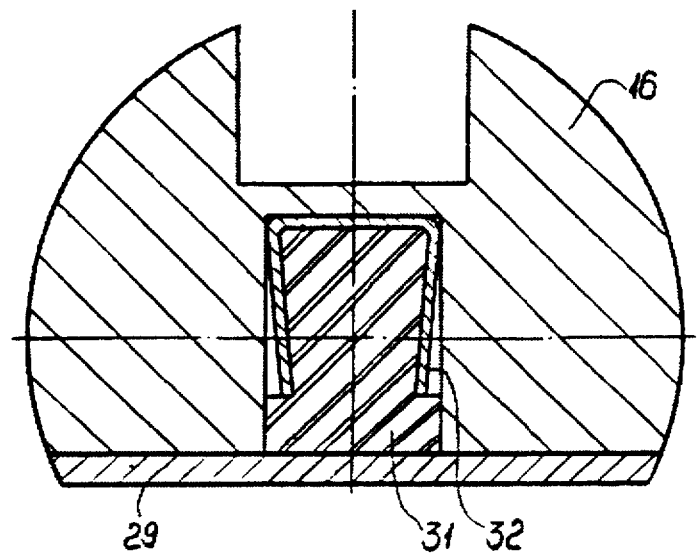
FIG. 19 is a cross section along J—J through a staple feed mechanism of FIG. 16.
Figure 20:
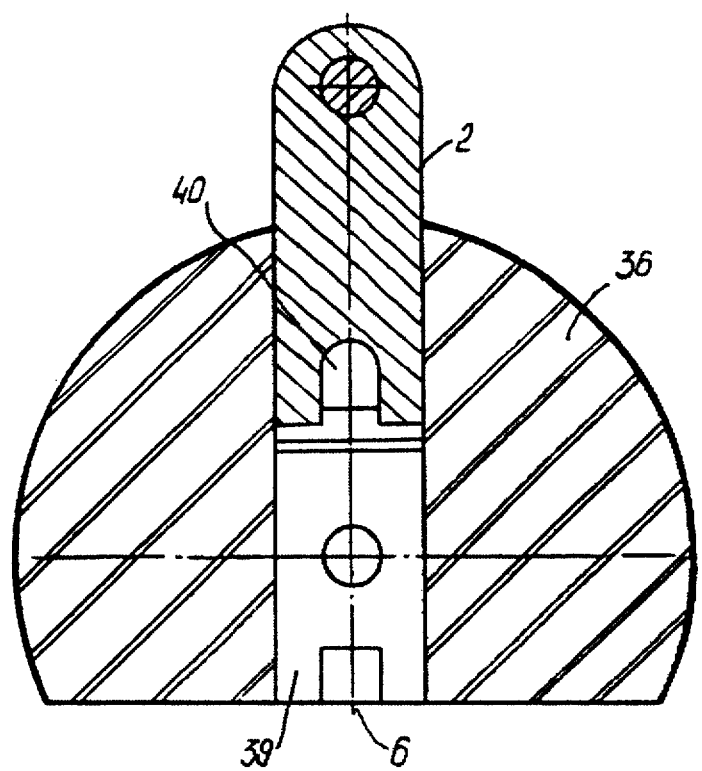
FIG. 20 is a cross section along M—M through an end cap mechanism of FIG. 16.
Figure 21:
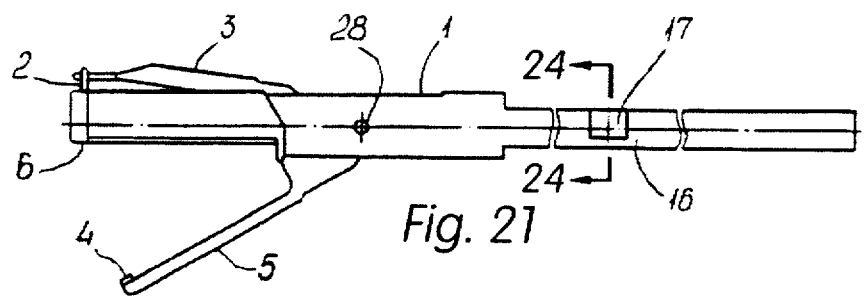
FIG. 21 is a side view of the staple magazine assembly.
Figure 22:
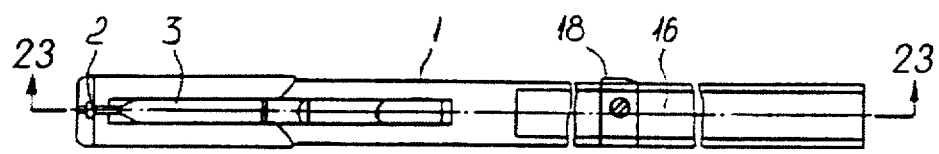
FIG. 22 is a top view of the staple magazine assembly of FIG. 21.
Figure 23:
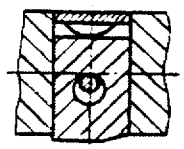
FIG. 23 is a cross section along Y—Y of FIG. 22.
Figure 24:
FIG. 24 is a cross section along Z—Z through a catch portion of FIG. 21.
Figure 25:
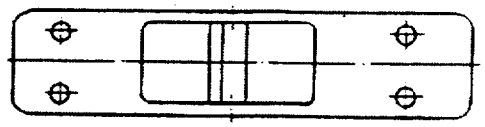
FIG. 25 is a top view of the handle.
Figure 26:
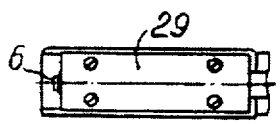
FIG. 26 is a bottom view of the cover.
Figure 27:
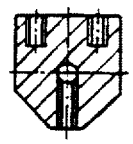
FIG. 27 is a cross section along Q—Q of FIG. 30.
Figure 28:
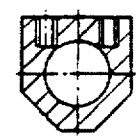
FIG. 28 is a cross section along R—R of FIG. 30.
Figure 29:
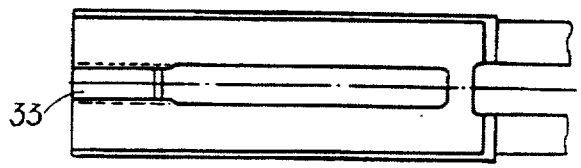
FIG. 29 is a bottom view of the magazine body.
Figure 30:
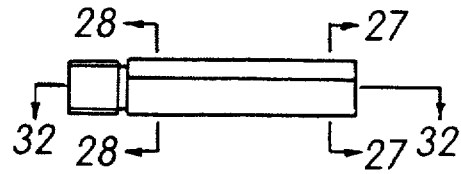
FIG. 30 is a side view of the magazine body.
Figure 31:
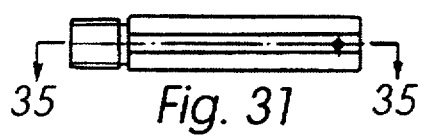
FIG. 31 is a top view of the magazine body.
Figure 32:
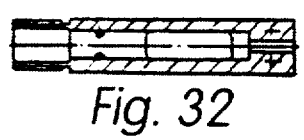
FIG. 32 is a cross section along P—P of FIG. 30.
Figure 33:
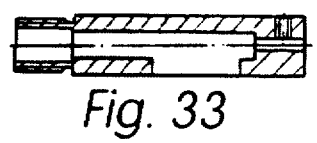
FIG. 33 is a cross section along S—S of FIG. 31.
Figure 34:
FIG. 34 is a cross section along BB—BB of FIG. 37.
Figure 35:
FIG. 35 is a cross section along T—T of FIG. 37.
Figure 36:
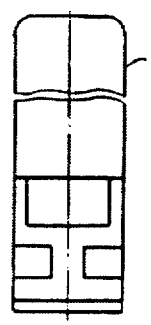
FIG. 36 is a front view of the handle.
Figure 37:
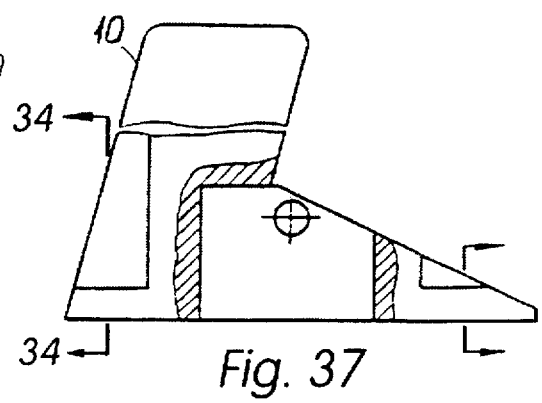
FIG. 37 is a side view of the handle.
Figure 38:
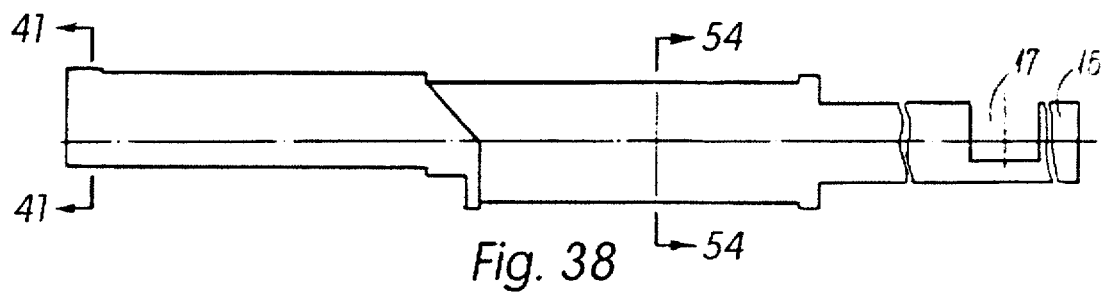
FIG. 38 is a side view of the magazine body.
Figure 39:
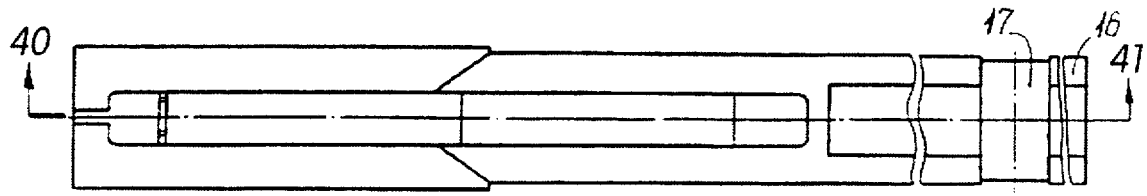
FIG. 39 is a top view of the magazine body.
Figure 40:
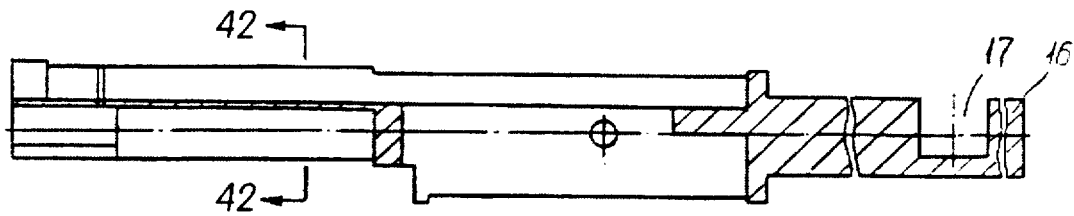
FIG. 40 is a cross section along W—W of the magazine body of FIG. 39.
Figure 41:
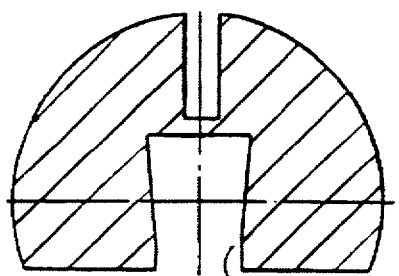
FIG. 41 is a cross section along U—U of FIG. 38.
Figure 42:
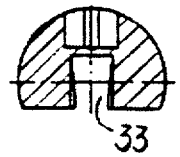
FIG. 42 is a cross section along X—X of FIG. 40.
Figure 43:
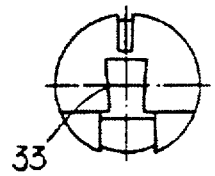
FIG. 43 is an end view of the magazine body.
Figure 44:
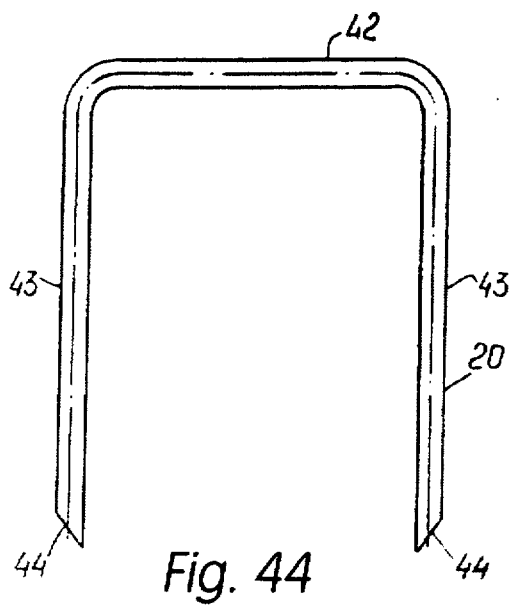
FIG. 44 is a front view of a staple.
Figure 45:
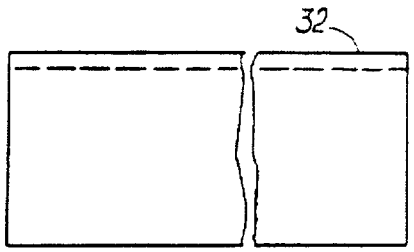
FIG. 45 is a side view of a trapezoidal sheet.
Figure 46:
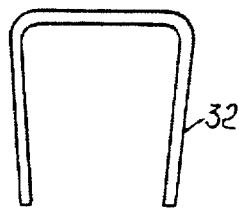
FIG. 46 is an end view of a trapezoidal sheet.
Figure 47:
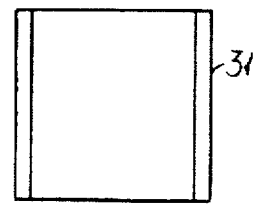
FIG. 47 is a top view of the block.
Figure 48:
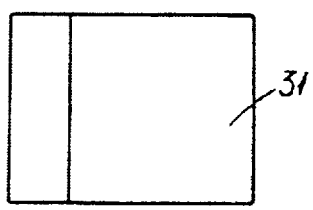
FIG. 48 is a side view of the block.
Figure 49:
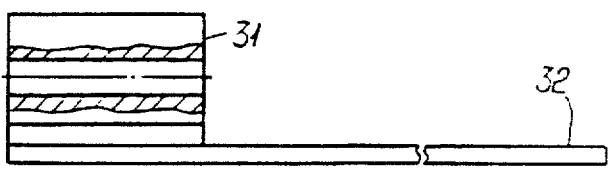
FIG. 49 is a cross section side view of the block and trapezoidal sheet.
Figure 50:
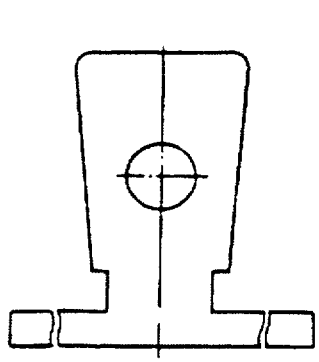
FIG. 50 is an end view of the cover and internal staple guide.
Figure 51:
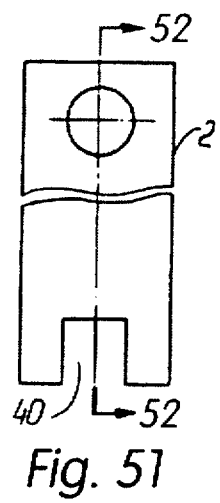
FIG. 51 is a front view of the pusher.
Figure 52:
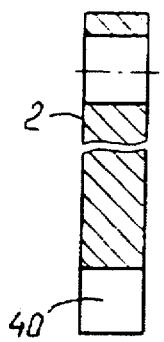
FIG. 52 is a cross section along CC—CC of FIG. 51.
Figure 53:
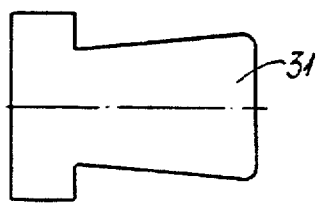
FIG. 53 is an end view of the block.
Figure 54:
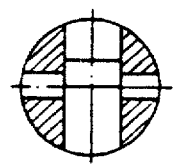
FIG. 54 is a cross section along V—V of FIG. 38.
Figure 55:
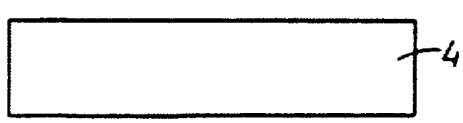
FIG. 55 is a front view of the former.
Figure 56:
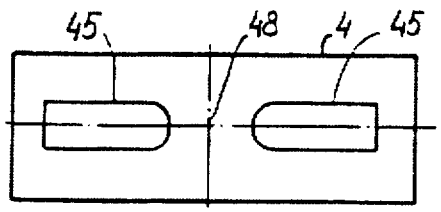
FIG. 56 is a top view of the former.
Figure 57:
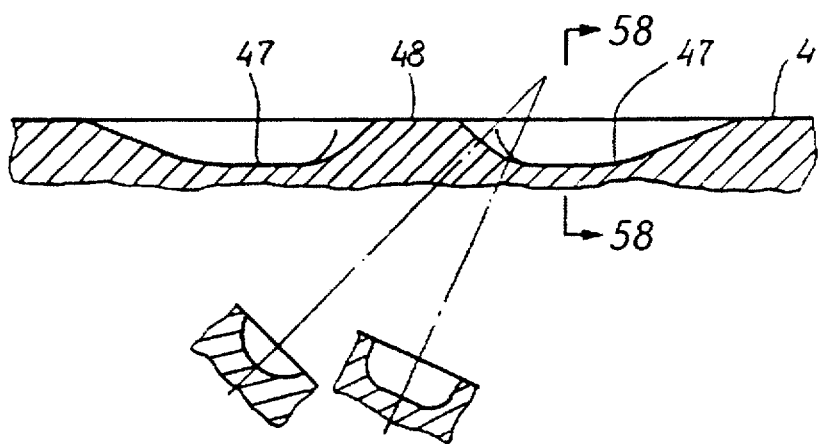
FIG. 57 is a cross section along N—N of FIG. 59.
Figure 58:
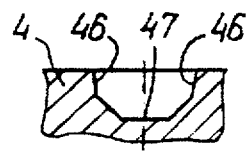
FIG. 58 is a cross section along O—O of FIG. 57.
Figure 59:
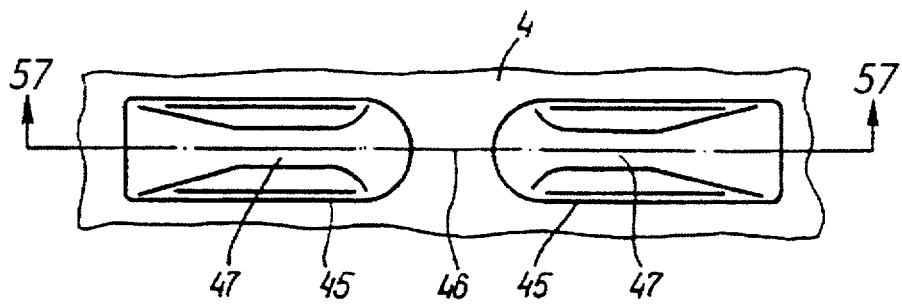
FIG. 59 is a detail top view of the former.

FIG. 1 shows a side view of a preferred surgical stapler embodiment of the present invention, for sequentially inserting and forming a single staple at a time. FIG. 1 shows the construction of the device. The outer diameter of the shaft of the stapler is 11 mm, for insertion in an 11 mm ID trochar sleeve. The construction of the device provides sealing, preventing the release of gas from, for example, an inflated abdominal cavity, by providing close tolerances between the outer surface of the stapler and the inner surface of the trochar sleeve. The construction also allows free rotation of the stapler within the trochar sleeve and rotational freedom of the stapling head with respect to the handle.

The mechanism at the tip of the device actually need be no wider than the staple and the necessary supporting sidewall. Thus, with a 3 mm staple, the width of the tip need only be 1–2 mm wider than the staple, or 4–5 mm total.

In this embodiment, the magazine is adapted to hold about 20 staples, although only minor changes relating to the characteristics of the staple feed advance mechanism are necessary in order to adapt the magazine for between 1 and about 200 staples. In this embodiment, the magazines are interchangeable, and a cartridge containing the desired quantity of staples may be selected by the surgeon immediately prior to use.

The stapler, because of the length and compliance of the arm holding the former member, can attach tissues having a range of thicknesses. The present stapler can accommodate tissues between 0.5–2.5 mm compressed thickness tissues for attachment.

The staple itself is formed from a surgical titanium wire, the preferable staple having a width (crossmember length) of 3 mm, a height (leg length) of 4 mm and a wire diameter of 0.2 mm. The present embodiment may accommodate staples having shorter legs, and a wire diameter as little as 0.15 mm. The staples may be formed in a standard manner, by bending a wire over a form having broken edges, to produce a "U" shaped structure having legs splayed outward at an angle of 105° from the crossmember.

The staples, while in the magazine, have their legs inwardly bent, having an angle with respect to the upper connecting portion of the staple of about 85°, thus forming a trapezoidal structure. In their unconstrained state the staples have an angle of about 105°. Therefore, the staples are held in place through a frictional force against the side-wall of the channel, pressed against the side wall by the inherent spring force of the titanium wire. The bending forces exerted on the staple legs while retained in the channel are such as to apply an elastic deformation force without plastically deforming the staple. Further, this bent leg configuration assists in ensuring that only a single staple is engaged for ejection at any time by the pushing element, because it is separated from the pack of staples behind it by the termination of the feed channel into the end cap. The end cap at the end of the feed channel has an area for expansion of the staple to a perpendicular (90°) angle of the legs to the top bridging portion. This area of expansion also provides a further force inhibiting the forward movement of the staple adjacent to the active staple, since only a single staple can be present in the area of expansion at any given time. Thus, the active staple is separated from the remaining staples and has a different configuration. When the active staple is removed, or more properly, on the upstroke of the pushing element, the adjacent staple is moved to the active position by the spring force, and its legs expand to a perpendicular state.

The surgical stapler consists of two major assemblies: first, a handle with a tube like body, possessing all necessary elements for functionality, provided in a manner adapted for a series of stapling operations, and second, a magazine filled with a plurality of staples, a pushing element for extracting staples from the stapler and pushing them towards the former. The staple magazine is replaceable and interchangeable, allowing multiple uses of the handle assembly with a disposable staple cartridge, which is inserted within the tube-like body of the handle. Of course, the handle may also be disposable, and integral with the cartridge.

The handle 10 is adapted for being comfortably held in a surgeon's hand. Thus, an ergonomic design is applied to make the instrument comfortable and functionally appropriate in use. This handle 10 is connected by means of a transversely oriented pin 13 to the trigger 11. The trigger 11 is also ergonomically designed, so that the handle 10 and trigger 11 are together optimized for repeated use in the surgeon's hand. The trigger 11 is functionally linked to the pushing element, so that a relative movement of the handle 10 toward the trigger 11, e.g., by squeezing them together, causes, through a mechanical linkage, the former 4, mounted on a former arm 5, to move to a position proximate to the lower aperture 6 and the pusher 2, linked to a pusher arm 3, to eject the active staple 20 through the tissue and toward the former 4.

The magazine assembly 1 is held in fixed position by a spring loaded catch 18 in spring recess 17, in the magazine body 16, inserted coaxially and engaging a proximal outer sleeve of the handle assembly through an aperture 18' in the wall of the tube. The spring loaded catch 18 must be depressed in order to be inserted or removed from the magazine assembly 1. When inserted, the magazine assembly 1 is placed coaxially inside the outer sleeve 15, and moves to an extended position when the catch 18 lines up with the aperture 18' in the wall of the proximal outer sleeve 14, to achieve a form lock.

The handle 10 is connected by screw fasteners to the handle body 9. Inside the handle body 9 is a displaceable member 7 with a return spring 8. The return spring 8 is a helical spring concentric around an elongated stock 12, which is fixed in place by a set screw 21 mounted in the handle body 9. The stock 12 is coaxial and inside the displaceable member 7. The displaceable member 7 is moved in response to a movement of the trigger 11 with respect to the handle 10. The trigger 11 has, at its upper end, a yoke 22 adapted to displace the displaceable member 7 without limiting its rotational freedom. The displaceable member 7 thus has rotational freedom of 360°.

The displaceable member 7 is rotatable about its long axis within the handle body 9, and is in fixed rotational orientation with respect to a rotatable collar 23. The displaceable member 7 has a pair of channels 24 which allow longitudinal displacement of the displaceable member 7 with respect to the rotatable collar 23, which is linked to a proximal outer sleeve 14, by set screws 25 which further sit in the pair of channels 24. The proximal outer sleeve 14 terminates a distance from the rotatable collar 23. At the termination of the proximal outer sleeve 14, the outer sleeve 15, which is fixed to the displaceable member 7, emerges. The proximal outer sleeve 14 and the outer sleeve 15 are coaxial and have the same diameter, thus ensuring a seal during endoscopic procedures. Prior to the termination of the proximal outer sleeve 14, there is an aperture 18' which is unobstructed by the displaceable member 7 therewithin.

The magazine assembly 1 has a magazine body 16, having a proximal portion in which the spring loaded catch 18 is placed. The magazine body 16 is of such configuration as to fit within the outer sleeve 15 and a portion of the proximal outer sleeve 14.

From the magazine body 16 emerges on a top aspect a pusher arm 3, having a return spring 26 pressing it outward.

From a bottom aspect of the magazine body 16 emerges a former arm 5, also having a return spring 27 pressing it outward. Both the former arm 5 and the pusher arm 3 pivot about an axle 28 within the magazine body 16.

The magazine body 16 is hollow in a distal portion, covered by a cover 29. The hollow section contains the staple feed mechanism. The staple feed mechanism consists of a helical staple feed spring 30 pressing against a block 31 having a trapezoidal sheet 32 elongated extension which slides within a staple channel 33, thus pushing the staples 19 within the channel 33. The trapezoidal sheet fits 32 around the block 31, and are held together by soldering. Alternatively, the block may be formed integral with a bent portion of the trapezoidal sheet. The staple feed channel 33 is oriented such that the top portion of the staples 19 are under the pusher arm 3.

The staple feed spring 30 and block 31 are held within the hollow section by the cover 29 which terminates at a distal portion in an inner staple guide 35, which, together with the hollow section, forms a three sided U-shaped trapezoidal aperture which is the staple feed channel 33, which terminates in a space 34 provided in an end cap 36. The end cap 36 has a first vertical recess 37, which forms the space 34, having a pair of vertical walls 38 and a depth of about the width of one staple 20, and certainly significantly less than two staples 19, 20. Thus, with a 0.2 mm staple width, the first vertical recess 37 is about 0.22 mm deep. The end cap 36 has a second vertical recess 39, for guiding the pusher 2, which is deeper and narrower than the first vertical recess 37. The second vertical recess 39 has a depth such that the pusher 2 does not interfere with the end of the magazine body 16, and thus clears the last staple 19 in the U-shaped trapezoidal aperture which is the staple feed channel 33. The pusher 2 is a rectangular block which slides within the second vertical recess 39. The bottom portion of the pusher 2 has a central recess 40 to provide clearance for upturned tips 44 of a staple 20 at the end of a stapling operation.

In operation, the trigger 11 is depressed and the outer sleeve 15 advances with respect to the staple magazine assembly 1, which is held by the spring loaded catch 18 in the aperture 18' of the proximal outer sleeve 14. The outer sleeve 15 initially presses against the former arm 5, which is pressed against the magazine body 16 and assumes an orientation parallel to the longitudinal axis of the staple magazine assembly 1. The tissues to be fastened are held between the former 4 at the end of the former arm 5 and the cover 29 on the bottom of the staple magazine assembly 1.

Further advance of the outer sleeve 15 rapidly presses the pusher arm 3 downward, against the magazine body 16, such that the pusher 2 is depressed fully, thereby expelling the active staple 20, which is deformed by the former 4. Further advance of the outer sleeve 15 has little effect, but provides an overtravel region which assures proper fastening.

The magazine assembly 1 is constructed as follows. The magazine assembly consists of a magazine body 16, which is securely connected to and covered with cover 29. Staples 19, having a "U" shape, are held in the magazine body 16 by the trapezoidal sheet 32 linked to the block 31 at the end of the staple feed spring 30 on one end, and the end cap 36 on the other end. The staples 19, 20 are confined in a channel 33 in the magazine assembly 1 formed by a magazine body 16, having a hollow trapezoidal space having the desired configuration, and an inner block which is the inner staple guide 35, to prevent rotational misalignment of staples 19 within the channel 33, also having a solid, roughly trapezoidal form with some clearance for ease of movement of the staple. The inner staple guide 35 is affixed to the block by screws 41. The defined space between the magazine body 16 and inner staple guide 35, having the staples 19, has a profile such that the end of the dependent legs of the fasteners 19, e.g. the wire ends, after being charged into the magazine assembly 1, are held constrained, having their dependent legs compressed toward each other, from their free-state "U" shape.

The magazine assembly 1 is charged by compressing the legs of the "U" shaped staples 19 together to provide clearance for insertion of the staple 19 into the channel 33 of the magazine body 16. Thus, with the end cap 36 removed, staples 19 are sequentially inserted into the channel 33, with care being taken to hold previously inserted staples 19 in place while a next staple 19 is inserted. The first staple inserted presses against the staple feed spring 30, and transmits the spring force, used to advance the staples, to the active staple 20 (most recently inserted), which is held in place by the end plate 36. Of course, other method o staple insertion are possible.

Thus, when inserted into the channel 33 cavity, the staples 19 have but a single degree of freedom, advancing along a horizontal or longitudinal axis of the stapler. The active staple 20 in the first vertical recess 37 has an additional degree of freedom. In addition to having an axis of movement along the longitudinal axis of the stapler, constrained by the end plate 36, it also has a movement along the vertical axis of the magazine assembly 1, which is defined by the first vertical recess 37 in the end plate 36, the pusher 2, and the lower aperture 6. The active staple 20 is prevented from falling out of the lower aperture 6 by the frictional forces (e.g. force locked) of the adjacent staple 19, pressed against it by the spring force, and the vertical walls 38 of the first vertical recess 37 in the end plate 36. Since the free expansion configuration of the staple 19, 20 has an angle of 105° between the top bridging portion 42 and the legs 43, the legs press outwardly against the vertical walls 38 of the first vertical recess 37. If necessary, the active staple 20 could also be held in place by a form lock system, having a mechanical linkage which releases the staple 20 as the pusher 2 begins advancing toward the former 4.

When the former 4 advances downward along the magazine assembly 1 vertical axis, it initially contacts the top bridging portion 42 of the staple 20, which bridges the two legs 43. In actuality, the pusher 2 has a central recess 40 or void in the middle, so that it applies a downward force at the lateral portions of the staple 20. The top bridging portion 42 will tend to bow slightly upward when the legs 43 are pressed together. The downward force is applied and distributed evenly to the staple legs 43 by the pusher 2.

The pusher 2 sits in the second vertical recess 39 in the end plate 36, such that it abuts the end of the staple channel 33, and thereby clears the staple 19 adjacent to the active staple 20. The pusher 2 does not eject the staple 19 adjacent to the active staple 20 because the width of the pusher 2 is carefully controlled to be equal to the full depth of the second vertical recess 39, which is approximately equal to the depth difference between the first vertical recess 37 and second vertical recess 39 plus the width of the active staple 20. The staple tips 44 are forced into the tissue matrix located between the staple tips 44 and the former 4, and the staple tips 44 begin to penetrate.

The pusher 2 continues to advance, such that the sharpened tips 44 of the legs 43 of the staple 20 emerge from the lower aperture 6 of the magazine assembly 1, aligned with the vertical axis thereof. In operation, the tissues to be attached lie in parallel planes immediately below the tips 44 of the advancing staple 20 and between the staple 20 and the former 4. The tips 44 of the staple 20 thus pierce the first tissue, emerge from the first tissue plane and pierce the second tissue plane. The tips 44 of the staple 20, upon emerging from the second tissue plane, are in contact with the former 2.

The former 2 is a hard steel element having a pair of asymmetrically curved indentations 45, which are aligned adjacent, with their axes parallel to each other. The indentations 45 are somewhat wider than a staple, with almost vertical sidewalls 46. The indentations 45 are placed such that the outer portions of each indentation are aligned with the expected positions of the staple tips 44. Thus, upon contacting the former 4, the staple tips 44 are curved toward each other, due to the downward force of the pusher 4 and the bending force of the surface of the indentation 45. As the staple 20 further advances, the tips 44 eventually reach the nadir 47 of the semi-ellipsoidally configured indentations 45, with the tips 44 advancing antiparallel, and the tips 44 then follow the curvature of the indentations 44 so that they turn and begin to advance upward. The radii of curvature of the former indentations 45 is selected such that the deformation exceeds the elastic deformation limits of the surgical titanium wire from which the staple 20 is formed. Thus, the staple legs 43 are plastically deformed and will substantially retain their bent shape after the former 4 is removed. The radius of curvature decreases toward the center 48 of the former 4, thereby causing the staple tips 44, as they emerge from the former 4, to be pointed upward. Because the staple 20, after being deformed by the former 4, has some resiliency, the former 4 is designed so that an optimal shape of the staple 20 is obtained after the former 4 is removed. This means that the former 4 should have a shape which has a conformation with a smaller radius of curvature than is ultimately desired, so that it rebounds to the desired shape. The ultimate shape of the staple 20 will, of course, depend on the staple material and configuration, the former 4 configuration, and the tissues being fastened.

The stapler is designed to accommodate a range of tissue thickness. First, the length of the staples 19, 20 may be selected by the surgeon prior to use, based on the properties of the tissue to be connected, although a 3 mm by 4 mm by 0.2 mm staple should suffice for most procedures. Second, the stapling process possesses a significant tolerance, such that the tissue thickness may vary substantially from 0.5 to 4.0 mm. In one embodiment according to the present invention, the former 4 may be displaced from its fully closed position during stapling in order to control the position of the staple tips 44 in the tissue after stapling.

The design according to the present embodiment is adapted in certain respects for small scale production, and of course it should be realized that the design may be advantageously modified for production on a larger scale without changing the fundamental aspects of operation according to the present invention.

The preferred embodiment of the present invention is fabricated completely from stainless steel, with the various springs being made from stainless steel adapted for use in springs, which may be fabricated in known manner from standard materials. The structural portions of the device according to the present invention may also be fabricated from plastics, with a particularly preferred material being Kaprylon®, with the exception of the springs, outer sleeve for depressing the former arm and pusher arm, the former and former arm and the pusher and pusher arm. The staple magazine body is particularly preferred to be formed of plastic. When constructed from various medically suitable plastics, the apparatus may be assembled using standard plastic fabrication techniques, including bonding, molding, fasteners and form lock configurations.

Example 2

The present embodiment employs an electrical power source located in the handle to provide power to an electromechanical transducer, formed as a linear-acting solenoid at the base of the core of the elongated shaft. The handle of the stapler has, mounted at the front, and extending downward, a member which activates an electrical switch. The switch preferably has a safety interlock which prevents accidental activation of the stapler during handling. The stapling head employed is essentially similar to the stapler of Example 1.

The present embodiment, shown in FIGS. 63 and 64 consists of a magazine assembly 1, an outer sleeve 15, a tube-like body 49, an electrical rotary motor 50, a handle 10, an electrical power source 51, an electrical connection system 52, a trigger button 53, an electrical switch 54, a helical gear 55, and a limit switch 56. The principal of operation of the present embodiment is the use of a motor 50, which drives a helical screw gear 55, causing a linear movement of a follower 57. The follower 57 is linked to an assembly which causes closure of the stapling head, as described above with respect to Example 1. Completion of a stapling operation is detected by a limit switch 56, which initiates a reversal of the motor 50, bringing the system to the starting position, which is detected by a second limit switch 58.

Alternatively, the helical gear may be replace with a dual-cut helical cam-follower system, to provide automatic return without need for reversing the motor. This arrangement further eliminates the need for one of the limit switches 56, particularly for detecting maximum excursion. Further, since the return stroke requires less torque than the excursion/stapling stroke, the return may be faster, e.g. a steeper helix, than the stapling stroke.

Further, the former may be positioned at a desired displacement from the closed position in order to control the position of the staple tips after stapling. Likewise, the pusher may be stopped short of full travel to control the position of the staple tips. Either of these may be accomplished by providing a clutch and mechanism to separate the movements of the pusher arm and the former arm, and controlling engagement of the clutch. When the pusher travel is controlled, the outer limit point may also be varied to effect the control, without a clutch.

In addition, an alternative embodiment is provided with its source of electrical power by a wire from a standard power supply or specially designed motor controller.

Example 3

In a second electrically powered embodiment of the present invention shown in FIG. 62, a sensor 59 is present which serves to prevent the insertion of staples 20 immediately on top of one another. This system works by incorporating a sensor 59 in the magazine assembly 1 generally according to Example 1, preferably near the lower aperture 6, near the point of exit of the staples 20, or alternatively in or near the former 4. Basically, a sensor 59 detects the change in electromagnetic properties of the medium surrounding the sensor 59, due to the presence of the surgical titanium wire of a previously inserted staple 20. A bulk conductivity sensor may also be employed, based on the difference in conductivity of the staple 20 and the tissues in which it is inserted, measurable due to the substantial length of the top bridging portion 42 of the staple 20. The system may be employed as a failsafe double insertion preventing system with automatic operation, or merely as an indicator to the surgeon. This same sensor may also be used to ensure that a staple is present at a sensed location, which may be obscured during use.

The stapler according to the present, sensor-equipped embodiment, includes a magazine assembly 1, an outer sleeve 15, a tube like body 49, a sensor 59, a handle 10, an electric connection system 52, an electric separator 61, a light source 60, a functional electric block 62 and an electric power source 51.

The device is essentially the apparatus according to either of Example 1 or Example 2. The sensor 59 is designed so that it reacts based on proximity of a previously inserted staple 20. In this embodiment, the staple proximity detector does not automatically prevent insertion, but rather has an annunciator to visually, e.g., the light source 60, or auditorily signal the surgeon of the proximity of a staple 20.

The electrical connection system 52 and the electric separator 61 act in conjunction to produce a signal, which is transmitted to the functional electric block 62 which produces an indication on trigger button 53 or any other known indicator, including an audible alarm, signaling the surgeon that he must relocate the stapling assembly in any direction, to prevent a chance of inadvertent repeated installation of a staple in the same place.

Example 4

In the present example, as depicted in FIG. 65, the motive force for the stapling mechanism is provided by a source of compressed air, e.g., a compressed gas canister 63 in the handle 10. The magazine assembly 1 is essentially identical to the embodiment according to Example 1. The compressed gas from the canister 63 is used to move a piston 64 in a cylinder 65, which, in turn, moves the displaceable member 7 with respect to the proximal outer sleeve 14. The trigger 11' actuates a valve 66, which causes compressed gas to enter the cylinder 65, moving the piston 64. The return stroke is implemented by a spring 67, acting against the piston 64, but a double acting cylinder 68 may alternatively be useful for this purpose. In either case, the gas must vent from the cylinder 65 at the completion of the stroke. The gas moves the piston 64 forward, until a vent valve 69 opens at the end of the stroke. The vent valve 69 vents the gas. In a double acting cylinder 68, simultaneously with venting of the actuator cylinder 65, the return cylinder 70 is supplied with the compressed gas by a control valve, causing the system to return to the starting position, at which time the gas in the return cylinder 70 vents through vent valve 69'. The gas preferably vents near the handle body 9.

The embodiment according to this pneumatic embodiment comprises a magazine assembly 1, an outer sleeve 15, a tube-like body 49, a return spring 67, a handle 10 assembly, a piston 64 in a cylinder 65 in the handle body 9', a vent valve 69, a compressed gas canister 63, a trigger 11' and an actuation valve 66.

In operation, the surgeon presses trigger 11', causing the actuation valve 66 to be opened. The actuation valve a predetermined quantity of gas to pass from the gas canister 63 into the cylinder 65 of handle body 9'. The compressed gas in the cylinder 65 acts on the piston 64, which further exerts a force which is transmitted to the displaceable member 7, closing the stapling mechanism as described above. The gas vents at the peak excursion of the piston 64, and the piston 64 returns to the starting position by means of a helical return spring 67 acting on the piston 64. The stapler is then in condition for a next stapling operation. The vent valve 69 is activated at the apex of the cylinder excursion by known means.

Example 5

The force for driving the stapling mechanism may also be hydraulic. The source of power for this hydraulic embodiment is a trigger 11 mounted first pump 73, although an external source of hydraulic power with a trigger actuated valve may be employed. Because hydraulic fluid 72 is incompressible, the use of a hydraulic systems also allows miniature hydraulic actuators to be incorporated in the stapling head. These miniature cylinders may be separately actuated and controlled, thus allowing independent control of the pusher, former, as well as articulation, auxiliary devices such as forceps, rinse valves, suturing devices, etc.

Figure 60:
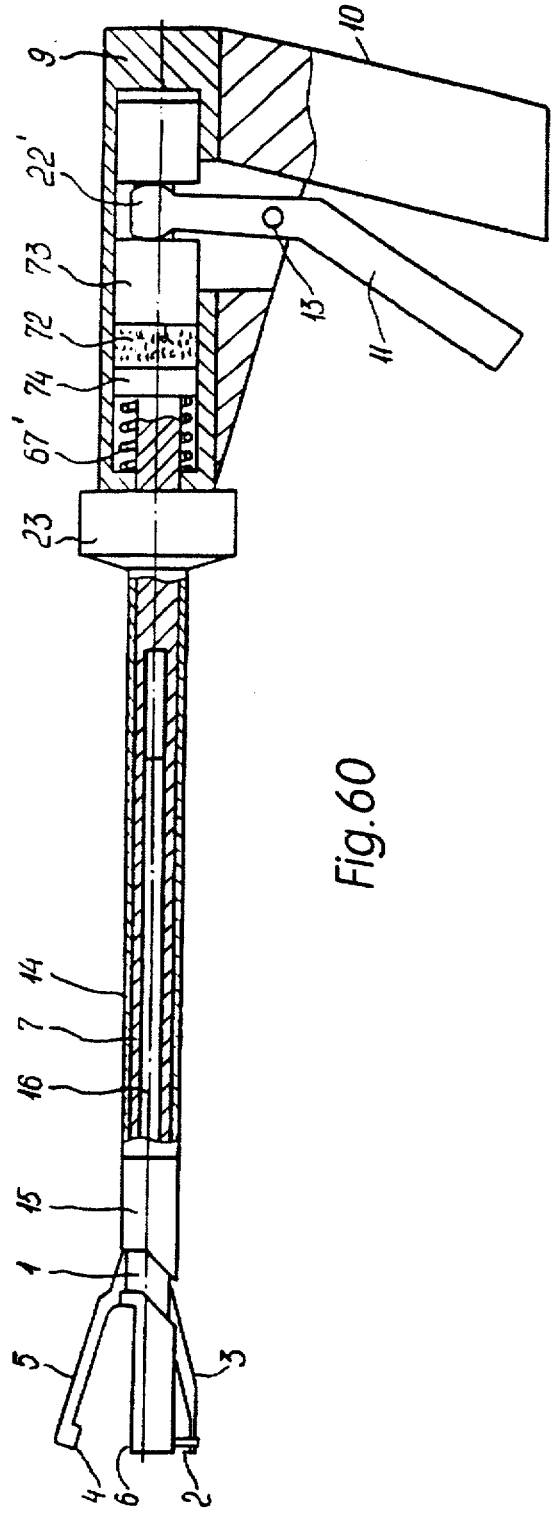
FIG. 60 is a partial cutaway side view of a hydraulic embodiment according to the present invention.

The magazine assembly 1 of the present embodiment, shown in FIG. 60 is essentially identical to the embodiment according to Example 1. The construction of the hydraulic embodiment comprises a magazine assembly 1, an outer sleeve 15, a tube-like body 49, hydraulic fluid 72, a handle 10, a return spring 67', a first pump 73 with piston 74, a handle body 9, a trigger 11 and a handle 10. The use of a fluid drive facilitates the use of flexible supply hose with a remote hydraulic actuator, which will allow a flexible endoscopic stapler with force feedback to the trigger. Hydraulic fluid is not generally vented, and therefore resides in a closed system. Of course, a biologically compatible fluid may be employed which may be vented within a body cavity.

Figure 61:
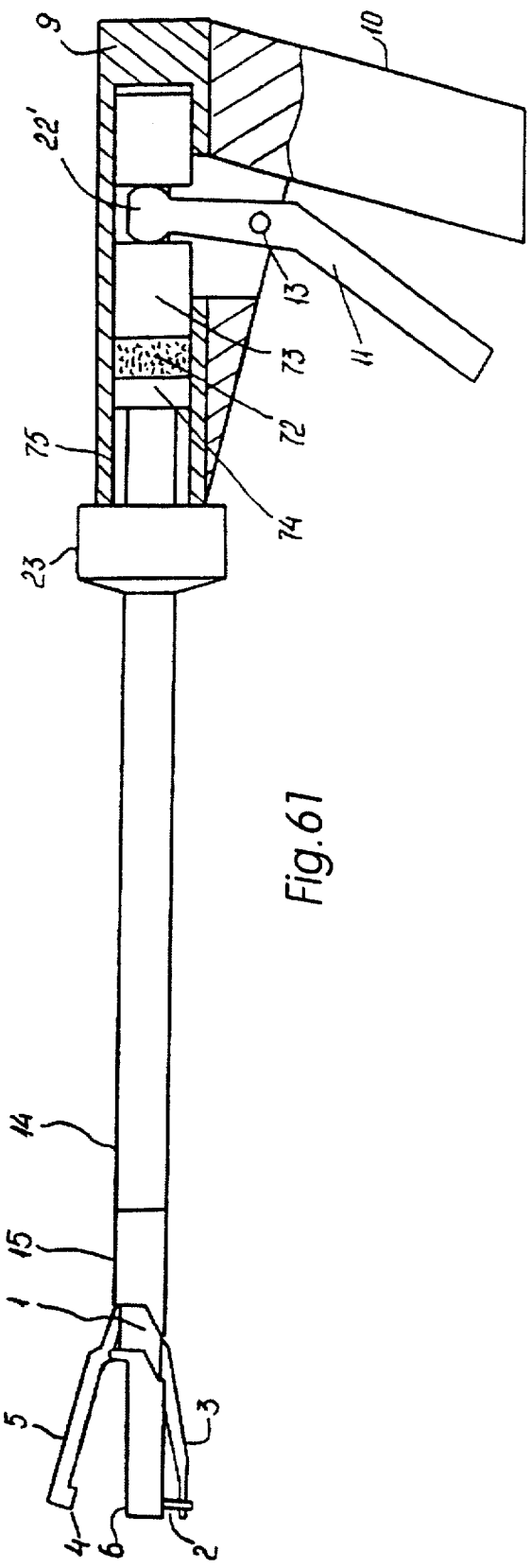
FIG. 61 is a partial cutaway side view of a hydraulic embodiment according to the present invention including a double-acting cylinder.

In an alternative embodiment, as shown in FIG. 61, the return spring 67' is replaced by a compressible gas 75 which, when compressed, exerts a return force on the piston 74.

Example 6

Figure 66:
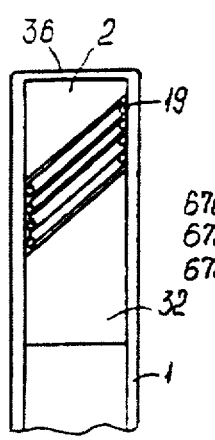
FIG. 66 shows a top view of an embodiment of a staple feed channel in which the staples are angulated with respect to the longitudinal axis of the staple feed channel.
Figure 67:
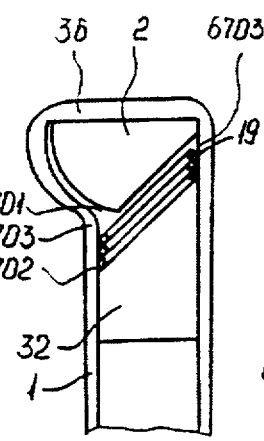
FIG. 67 shows a top view of an embodiment of a staple feed channel in which staples are angulated with respect to the longitudinal axis of the staple feed channel and rotate to a position perpendicular to the staple feed channel for insertion.

In order to reduce the width of the stapling device, the staple in the feed channel may be skewed, as shown in FIGS. 66 and 67. The staples in the guide are inclined with respect to the feed axis, in order to reduce the width of the device. At the tip of the device, the staple may be inserted at the inclined angle, as shown in the configuration of FIG. 66, or shifted into a position orthogonal to the feed axis, as shown in the configuration of FIG. 67.

In the embodiment according to FIG. 67, the staple legs need not be inwardly bent, in order to ensure reliable feed. The skew of the staples may provide the necessary differentiation to ensure a reliable feed. The staple angulation zone 6701 may be separated from the staple feed zone 6702 by a pair of ridges 6703, 6703'.

In order to reduce the height of the mechanism, staples may be inclined vertically, and inserted along an inclined axis or vertically realigned. When inserted inclined, the staple press also moves along an inclined axis, reducing the vertical travel distance. While the inclination may be at any angle, an inclination of 30° is preferred.

Example 7

Figure 68:
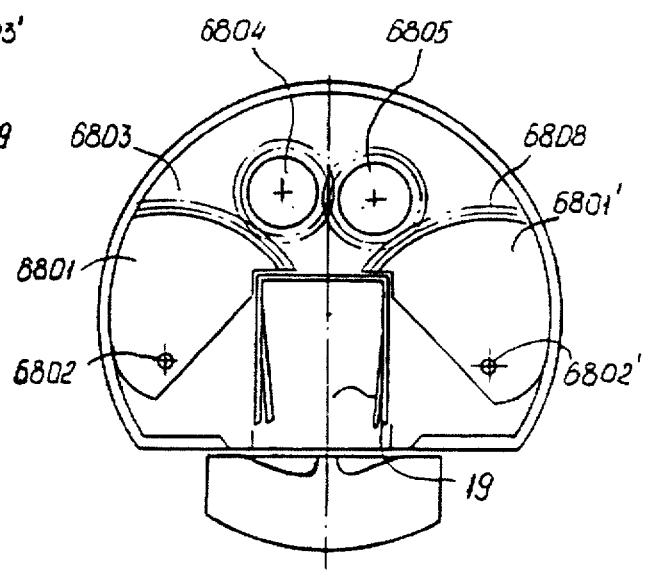
FIG. 68 shows a detail cross section through a staple insertion portion of an embodiment of a stapler in which sector gears, pivoting about points lateral to the staple feed channel eject the staple.
Figure 69:
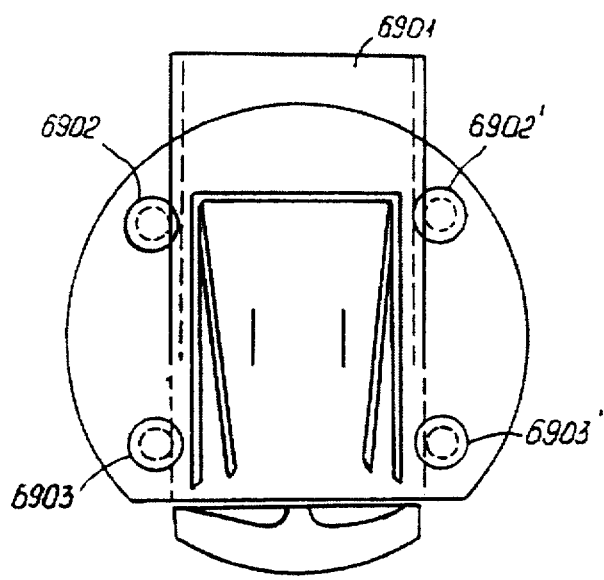
FIG. 69 shows a detail cross section through a staple insertion portion of an embodiment in which the pusher is displaced by sets of gears placed lateral to the staple feed channel.

The staple ejection mechanism may be provided as a low profile mechanism, as shown in FIGS. 68 and 69. As shown in FIG. 68, a pair of sector gears 6801, 6801', which respectively rotate about axes 6802, 6802', located laterally to the staple feed channel. The sector gears eject the staple 19 in the active region, while retaining the staples 20 in the feed channel. The rotating sector gears 6801, 6801' have teeth which enmesh. These sector gears may be driven by an axially rotating shaft or by way of a gear linkage 6804, 6805.

A low profile mechanism may also be provided by a linear acting pusher 6901, as shown in FIG. 69. The pusher 6901 is displaced by sets of gears 6902, 6902' and 6903, 6903'. This arrangement eliminates the pusher arm, and thus may reduce the size of the mechanism. This embodiment may also be used with a skewed or inclined staple, further reducing the height or width of the stapler.

Example 8

The apparatus according to Example 1, including staples having dimensions of 0.2×3×4 mm, having 30 staples per magazine, was used to anastomose healthy stomach and thin gut in a procedure known as a gasteroenteroanastomosis, to bypass the pyloric sphincter. The staples were inserted in either a single line of staples or two adjacent rows of staples. A total of 50 experiments were performed using the stapler, on fresh cadavers.

In the procedure, a 50 mm horizontal incision was made in the left lower quadrant, and the tissues dissected, exposing the stomach. The lower posterior wall of the stomach was exposed, and a longitudinal incision made. In addition, a portion of descending duodenum, on the posterior wall of the abdominal cavity was also exposed, and a longitudinal incision was made. The duodenum was then brought to a position near the gastric incision. The two incisions were approximately the same length. In order to fix the tissues with respect to the stapler, forceps are employed to provide traction to the tissue and hold the layers together. The walls of the two lumens were everted, mucosal layers touching, and the anterior walls of the incisions were initially stapled from top to bottom in a line approximately 3 mm from the cut edges. A second row of staples was then inserted next to the first, approximately 2 mm distal from the cut edge from the first row of staples, thus being approximately 5 mm from the cut edge. Next, the posterior walls were joined midway through the incisions, from top edge to middle. For this portion, the stomach wall incision was held in traction at an angle of about 20°–30° from the first incision. Finally, the incisions were closed by stapling from bottom edge to middle, completing the reanastomosis, in triangular fashion, to help ensure patency of the lumen. The outer row of staples was applied parallel to the incision, spaced every 5 mm. The inner row of staples was also spaced every 5 mm, aligned between the gaps in the outer row, in so-called "chess fashion".

In the above procedure, the tissues were cleanly and strongly connected. No cutting of the tissues by the stapling process was noted. Prior to closing the incision, the strength of the anastomosis was determined by palpation and gentle traction, and the closures were found to be strong. The closure was visually inspected, and the serosa were properly aligned. After the closure was completed, the small bowel was filled with a liquid. No leakage was noted of liquid from the incision.

The stapler according to the present invention allows wound closure at or near the incision edges, in the case of jagged edges, and the formation of comers and the use of controlled tension between staples in a closure, which helps to maintain the patency of the lumen of anastomosed organs.

It should be understood that the preferred embodiments and examples described herein are for illustrative purposes only and are not to be construed as limiting the scope of the present invention, which is properly delineated only in the appended claims.

What is claimed is:

1. A stapler, comprising:
   (a) a staple advancing system for applying an advancing force to a plurality of "U" shaped staples;
   (b) a guide, for maintaining said plurality of "U" shaped staples parallel to each other along a feed axis, said guide having a channel cross section including a horizontal top portion, substantially perpendicular to said feed axis, and two semi-vertical portions below said horizontal top portion, each having a plane oriented downwardly inward at such an angle which does not cause plastic deformation of said "U" shaped staples inserted in said guide, said guide having an open end wherein said semivertical portions merge with walls having vertical portions which are substantially aligned with a vertical axis;
   (d) a lower aperture, aligned with respect to said feed axis with said vertically aligned walls; and
   (e) a displaceable staple ejector, for displacing one of said "U" shaped staples proximate to said open end through said lower aperture, without displacing an adjacent "U" shaped staple.

2. The stapler according to claim 1, further comprising:
   (a) a mechanism producing an actuation signal;
   (b) an actuation signal transmission system;
   (c) a displaceable former, for plastically deforming staple ends, said former being displaceable between a first position in which the former is substantially displaced along said vertical axis from said lower aperture and a second position in which the former is substantially proximate to said lower aperture along said vertical axis; and
   (d) control means for displacing said former from the first position to said second position and for displacing said staple ejector.

3. The stapler according to claim 2, wherein said actuation signal transmission system comprises a system selected from the group consisting of mechanical, electrical, pneumatic and hydraulic.

4. The stapler according to any of claim 1, wherein said staple advancing system for applying an advancing force comprises a helical spring pressing against a staple feeding member.

5. The stapler according to any of claim 1, further comprising a former arm and an ejector arm, said former arm and said ejector arms each being hinged with a return spring at a point distant from said open end, wherein said control means comprises a displaceable sleeve riding over a portion of said pusher arm and a portion of said former arm, depressing said pusher arm and said former arm during displacement.

6. The stapler according to any of claims 1–3, further comprising a former arm and an ejector arm, said former arm and said ejector arms each being hinged with a return spring at a point distant from said open end, wherein said control means comprises a displaceable sleeve riding over a portion of said pusher arm and a portion of said former arm, depressing said pusher arm and said former arm during displacement, and wherein said staple advancing system for applying an advancing force comprises a helical spring pressing against a staple feeding member.

7. The stapler according to any of claim 1, further comprising an end guide aligned with said vertical axis, a first recess aligned with said vertical axis and a second recess, deeper than said first recess, aligned with said vertical axis, said lower aperture being aligned with said vertical axis and said displaceable staple ejector being displaceable along said vertical axis in said second recess, and guided thereby.

8. The stapler according to any of claim 1, wherein a staple in said guide has its legs elastically deformed to conform to the trapezoidal profile of said guide, and a staple exiting said longitudinal guide into said open end has its legs projecting parallel to one another, abutting said vertical portions.

9. The stapler according to any of claim 1, further comprising a plurality of staple guides and a plurality of lower apertures, for providing a plurality of simultaneously inserted staples.

10. The stapler according to any of claim 1, further comprising a selectively engageable lock to prevent ejection of a staple.

11. A method of attaching sheet-like materials, comprising providing a stapler comprising:

(a) a mechanism producing an actuation signal;

(b) an actuation signal transmission system;

(c) a staple cartridge having (i) a staple advancing system for applying an advancing force to a plurality of "U" shaped staples;

(ii) a guide, for maintaining said plurality of "U" shaped staples parallel to each other along a feed axis, said guide having a channel cross section including a horizontal top portion, substantially perpendicular to said feed axis, and two semi-vertical portions below said horizontal top portion, each having a plane oriented downwardly inward at such an angle which does not cause plastic deformation of said "U" shaped staples inserted in said guide, said guide having an open end wherein said semivertical portions merge with walls having vertical portions which are substantially aligned with a vertical axis;

(iii) a lower aperture, aligned with respect to said feed axis with said vertically aligned walls; and (iv) a displaceable staple ejector, for displacing one of said "U" shaped staples proximate to said open end through said lower aperture, without displacing an adjacent "U" shaped staple;

placing the sheets to be attached along the vertical axis of the staple ejector, between the staple and the former;

(d) a displaceable former, for plastically deforming staple ends, said former being displaceable between a first position in which the former is substantially displaced along said vertical axis from said lower aperture and a second position in which the former is substantially proximate to said lower aperture along said vertical axis; and (e) control means for displacing said former from the first position to said second position and for displacing said staple ejector;

displacing said former from the first position to said second position; and displacing said staple ejector.

12. A method of attaching sheets according to claim 11, wherein said former is displaced in a first phase to compress the sheets and the staple ejector is displaced in a second phase to eject said "U" shaped staple and staple said sheets.

13. A method according to claim 11 further comprising the step of displacing said staple ejector away from said former along said vertical axis in a third phase, during which a staple is released from said guide into said open end, with its legs springing outward to contact said vertically aligned walls.

14. The method according to claim 11, wherein said actuation signal transmission system comprises a system selected from the group consisting of mechanical, electrical, pneumatic and hydraulic.

15. The method according to any of claim 11, further comprising the step of applying said advancing force by means of a helical spring pressing against a staple feeding member.

16. The method according to any of claim 11, further comprising providing a former arm and an ejector arm, said former arm and said ejector arms each being hinged with a return spring at a point distant from said open end, wherein said control means comprises a displaceable sleeve riding over a portion of said pusher arm and a portion of said former arm, said displacing step comprising depressing said pusher arm and said former arm by displacing said sleeve.

17. The method according to any of claim 11, further comprising providing a former arm and an ejector arm, said former arm and said ejector arms each being hinged with a return spring at a point distant from said open end, wherein said control means comprises a displaceable sleeve riding over a portion of said pusher arm and a portion of said former arm, said displacing step comprising depressing said pusher arm and said former arm by displacing said sleeve, and wherein said staple advancing system for applying an advancing force comprises a helical spring pressing against a staple feeding member.

18. The method according to any of claim 11, further comprising providing an end guide aligned with said vertical axis, a first recess aligned with said vertical axis and a second recess, deeper than said first recess, aligned with said vertical axis, said lower aperture being aligned with said vertical axis and said displaceable staple ejector being displaceable along said vertical axis in said second recess, and guided thereby.

19. The method according to any of claim 11, further comprising the step of elastically deforming the legs of a staple in said guide to conform to the trapezoidal profile of said guide, and expelling a staple from said longitudinal guide into said open end so that its legs projecting parallel to one another, abutting said vertical portions.

* * * * *